(12) United States Patent
Barritault

(10) Patent No.: US 11,351,190 B2
(45) Date of Patent: Jun. 7, 2022

(54) COMPOSITION FOR TREATING TISSUE LESIONS

(71) Applicants: Denis Barritault, Paris (FR); ORGANES TISSUS REGENERATION REPARATION REMPLACEMENT—OTR3, Paris (FR)

(72) Inventor: Denis Barritault, Paris (FR)

(73) Assignees: ORGANES TISSUS REGENERATION REPARATION REMPLACEMENT—OTR3, Paris (FR); Denis Barritault, Paris (FR)

(*) Notice: Subject to any disclaimer, the term of this patent is extended or adjusted under 35 U.S.C. 154(b) by 0 days.

(21) Appl. No.: 15/577,736

(22) PCT Filed: May 26, 2016

(86) PCT No.: PCT/EP2016/061906
§ 371 (c)(1),
(2) Date: Nov. 28, 2017

(87) PCT Pub. No.: WO2016/189088
PCT Pub. Date: Dec. 1, 2016

(65) Prior Publication Data
US 2018/0125880 A1 May 10, 2018

(30) Foreign Application Priority Data
May 28, 2015 (EP) .................................... 15305807

(51) Int. Cl.
| A61K 31/737 | (2006.01) |
| A61K 9/00 | (2006.01) |
| A61K 47/36 | (2006.01) |
| A61P 17/02 | (2006.01) |
| A61K 35/19 | (2015.01) |
| A61K 38/18 | (2006.01) |
| A61K 35/32 | (2015.01) |
| A61K 35/35 | (2015.01) |
| A61K 9/08 | (2006.01) |

(52) U.S. Cl.
CPC ............ *A61K 31/737* (2013.01); *A61K 9/006* (2013.01); *A61K 9/0019* (2013.01); *A61K 9/0024* (2013.01); *A61K 9/0043* (2013.01); *A61K 9/0053* (2013.01); *A61K 9/0078* (2013.01); *A61K 9/08* (2013.01); *A61K 35/19* (2013.01); *A61K 35/32* (2013.01); *A61K 35/35* (2013.01); *A61K 38/1825* (2013.01); *A61K 38/1858* (2013.01); *A61K 38/1866* (2013.01); *A61K 47/36* (2013.01); *A61P 17/02* (2018.01); *A61K 2300/00* (2013.01)

(58) Field of Classification Search
CPC .. A61K 31/737; A61K 9/0019; A61K 9/0024; A61K 9/0043; A61K 9/0053; A61K 9/006; A61K 9/0078; A61K 9/08; A61K 5/19; A61K 35/32; A61K 35/35; A61K 38/1825; A61K 38/1858; A61K 38/1866; A61K 47/36; A61K 2300/00; A61K 35/12; A61K 38/18; A61P 17/02; A61P 19/02; A61P 1/00
See application file for complete search history.

(56) References Cited

U.S. PATENT DOCUMENTS

| 7,998,922 | B2 * | 8/2011 | Barritault ................. A61P 9/00 514/1 |
| 8,790,631 | B2 * | 7/2014 | Barritault ................. A61K 8/73 424/488 |
| 2001/0021758 | A1 * | 9/2001 | Barritault ............ C08B 37/0021 526/287 |
| 2001/0023246 | A1 | 9/2001 | Barritault et al. |
| 2002/0098564 | A1 | 7/2002 | Conklin et al. |
| 2004/0131583 | A1 | 7/2004 | Barritault et al. |
| 2006/0257449 | A1 * | 11/2006 | Billy ...................... A61L 27/46 424/426 |

(Continued)

FOREIGN PATENT DOCUMENTS

| BR | PI0805852 A2 | 8/2010 |
| FR | 2781485 A1 | 1/2000 |

(Continued)

OTHER PUBLICATIONS

Medicine.net, obtained online at https://www.medicinenet.com/script/main/art.asp?articlekey=9695, downloaded on Oct. 22, 2018. (Year: 2004).*
Tong et al., Diabetes, 61, 2633-2641. (Year: 2012).*
Tong et al., Wound Rep Reg, 16, 294-299. (Year: 2008).*
Dash et al., Rejuvenation Research, 12(5), pp. 359-366. (Year: 2009).*
Frescaline, Guilhem, et al. "Glycosaminoglycans mimetics potentiate the clonogenicity, proliferation, migration and differentiation properties of rat mesenchymal stem cells." Stem cell research 8.2 (2012): 180-192. (Year: 2012).*

(Continued)

*Primary Examiner* — Abigail Vanhorn
(74) *Attorney, Agent, or Firm* — Kenealy Vaidya LLP

(57) ABSTRACT

Some embodiments are directed to a pharmaceutical composition including a biocompatible polymer in association with a eukaryotic cell, a platelet extract and/or lysate, or a growth factor, to be used as a drug for the prevention and/or treatment of tissue lesions. Some other embodiments are also directed to a pharmaceutical kit which includes a biocompatible polymer in association with a eukaryotic cell for the prevention and/or treatment of tissue lesions. Some other embodiments are also directed to the use of a pharmaceutical composition including a biocompatible polymer in association with a eukaryotic cell, a platelet extract and/or lysate, or a growth factor, for manufacturing a drug for the treatment of tissue lesions. Some other embodiments can be used in particular in the veterinary and pharmaceutical fields.

8 Claims, No Drawings

(56) References Cited

U.S. PATENT DOCUMENTS

| | | | |
|---|---|---|---|
| 2007/0141020 A1 | 6/2007 | Barritault et al. | |
| 2011/0243881 A1 | 10/2011 | Barritault et al. | |
| 2014/0302510 A1* | 10/2014 | Papy-Garcia | A61K 31/713 435/6.12 |
| 2018/0161372 A1* | 6/2018 | Bernaudin | A61K 31/737 |

FOREIGN PATENT DOCUMENTS

| | | |
|---|---|---|
| FR | 2794649 A1 | 12/2000 |
| KR | 101401273 B1 | 5/2014 |
| WO | 9526737 A1 | 10/1995 |
| WO | WO03/101201 A1 | 12/2003 |

OTHER PUBLICATIONS

Walter, Dirk H., et al. "Intraarterial administration of bone marrow mononuclear cells in patients with critical limb ischemia: a randomized-start, placebo-controlled pilot trial (PROVASA)." Circulation: Cardiovascular Interventions 4.1 (2011): 26-37. (Year: 2011).*

Mullangi, C., et al., "New Agent, Regenerating Agent (RGTA) and Bone Marrow Derived CD34+ Lineage Stem Cells Transplantation for the Treatment of Acute Myocardial Infarction," Ind. J. Thoracic Cardiovasc. Surg. 2006;22 (1):71.

Chevalier, F., et al., "Glycosaminoglycan Mimetic Improves Enrichment and Cell Functions of Human Endothelial Progenitor Cell Colonies," Stem Cell Res. 2014;12(3):703-715.

Guilheim, F., et al., "Glycosaminoglycan Mimetic Associated to Human Mesenchymal Stem Cell-Based Scaffolds Inhibit Ectopic Bone Formation, but Induce Angiogenesis In Vivo," Tissue Engineering Part A 2013; 19 (13-14):1641-1653.

Tamarat, R., "ANTHOS Project," Mar. 1, 2015, p. 1, XP055219851, URL:http:///www.irsn.fr/EN/Research/Research-organisation/Research-programmes/ANTHOS-project/Pages/ANTHOS-project.aspx.

Tadanori, M., et al., "Platelet Rich Plasma Extract Promotes Angiogenesis Through the Angiopoietin1-Tie2 Pathway," Microvasc. Res. 2013;89:15-24.

International Search Report and Written Opinion for PCT Patent App. No. PCT/EP2016/061906 (dated Sep. 5, 2016) with English language translation of the ISR.

Van Neck et al., Heparan Sulfate Proteoglycan Mimetics Promote Tissue Regeneration: An Overview chapter 4 in Tissue Regeneration—From Basic Biology to Clinical Application ISBN 978-953-51-0387-5, edited by Jamie Davies.

Mangoni M et al., "Differential Effect Triggers By A Heparan Mimetic of the RGTA Family Preventing Oral Mucositis Without Tumor Protection," Int. J. Radiation Oncology Biol. Phys. 2009,74,1242-1250.

Yue X-L et al., "Insights on a new path of pre-mitochondrial apoptosis regulation by glycoaminoglycan mimetic," Cell Death and Differentiation 2009, 1-12.

Desgranges et al., "A substituted dextran enhances muscle fiber survival and regeneration in ischemic and denervated rat EDL muscle," FASEB J. Apr. 1999; 13(6):761-766.

Larramendy-Gozalo, C. D. et al., "Comparison of CR36, a new heparan mimetic, and pentosan polysulfate in the treatment of prion diseases," J Gen Virol. 2007, 88:1062-1067.

Albanese, P., et al., "Glycosaminoglycan mimetics-induced mobilization of hematopoietic progenitors and stem cells into mouse peripheral blood: Structure/function insights," Experimental Hematology 2009;37:1072-1083.

Mullangi, C., et al., "New agent, regenerating agent (RGTA) and bone marrow derived CDM34+ lineage stem cells transplantation for the treatment of acute myocardial infarction," Coronary 2006;22:71.

Yamauchi, H. et al., "New agents for the treatment of infarcted myocardium," FASEB J. 2000 (14): 2133-2134.

Knighton, D. R., et al., "Classification and treatment of chronic nonhealing wounds. Successful treatment with autologous platelet-derived wound healing factors (PDWHF)," Ann Surg. Sep. 1986; 204(3): 322-330.

Everts, P.A.M et al., "Differences in platelet growth factor release and leucocyte kinetics during autologous platelet gel formation," Transf. Med., 2006, 16(5), 363-368.

Everts, P.A.M et al.,"Is the Use of Autologous Platelet-Rich Plasma Gels in Gynecologic, Cardiac, and General, Reconstructive Surgery Beneficial ?" Pharmaceutical Biotechnology, 2012, vol. 13N°13.

Ikeda, Y., et al., "Synthesis and biological activities of a library of glycosaminoglycans mimetic oligosaccharides," Biomaterials 2011;32:769-776.

Khammari-Chebbi, C., et al., "Étude pilote d'un nouvel agent de thérapie matricielle (RGTA OTR4120®) dans les ulcères de cornée et les dystrophies cornéennes rebelles," J Fr Ophtalmol. May 2008;31(5):465-71.

Frescaline, G., et al., Tissue Eng Part A. Jul. 2013;19(13-14):1641-53. doi: 10.1089/ten.TEA.2012.0377.

Coudry, V., et al. Long-Term Follow-up of Superficial Digital Flexor Tendonitis Treated by a Single Intralesional Injection of a ReGeneraTing Agent in 51 Horses Journal of Equine Veterinary Science 34 (2014) 1357-1360.

Meddahi, A., et al., "Pharmacological studies of RGTA11, a heparan sulfate mimetic polymer, efficient on muscle regeneration," J Biomed Mater Res 60:497-501 2002.

Alexakis, C., et al., "Reveral of abnormal collagen production in Crohn's disease intestinal biopsies treated with regenerating agents," Gut 2004;53:85-90.

Alexakis, C., et al., "Heparan mimetic regulates collagen expression and TGF-β1 distribution in gamma-irradiated human intestinal smooth muscle cells," FASEB J. 2001, 15,1546-1554.

Yue X-L, Lehri S, Li P, Barbier-Chassefière V, Petit V, Huang Q-F, Albanese P, Barritault D, Caruelle J-P, Papy-Garcia D and Morin C. Insights on a new path of pre-mitochondrial apoptosis regulation by a glycosaminoglycan mimetic.; Yue X-L et al, Cell Death and Differentiation, 2009, 1-12.

Soleimani, M., et al., "A protocol for isolation and culture of mesenchymal stem cells from mouse bone marrow," S. Nat Protoc. 2009;4(1):102-106.

Hernigou, P., et al., "Cancer risk is not increased in patients treated for orthopaedic diseases with autologous bone marrow cell concentrate," J Bone Joint Surg Am. 2013;95:2215-2221.

David Carnicer, mémoire de recherche "Preliminary report: ultrasonographic evolution of tendon lesions treated with RGTA in horses," Feb. 2009, école nationale vétérinaire de Maison Alfort.

Pechayre, M., et al., "Comparison du Traitement des Tendinopathies Chez Le Cheval de Course Par Le RGTA Par La Moelle Osseuse (MO)," S0704, congrès AVAC, Dec. 2-4, 2011.

Morvan, F., et al., "An Engineered Biopolymer Prevents Mucositis Induced by 5-Fluorouracil in Hamsters," Am J Pathol. Feb. 2004; 164(2):739-46.

Escartin, Q., et al., "A new approach to treat tissue destruction in periodontitis with chemically modified dextran polymers," FASEB J. Apr. 2003; 17(6):644-51.

Mullangi, C., et al., "New agent (RGTA) and bone marrow derived CD34+ lineage stem cells transplantation for the treatment of acute myocardial infarction," Indian Journal of Thoracic and Cardiovascular Surgery, vol. 22, No. 1, Mar. 2006.

Chevalier, F., et al., "Glycosaminoglycan mimetic improves enrichment and cell functions of human endothelial progenitor cell colonies," Stem Cell Research, vol. 12, No. 3, Mar. 10, 2014, p. 703-715.

Frescaline, G., et al., "Glycosaminoglycan mimetic associated to human mesenchymal stem cell-based scaffolds inhibits ectopic bone formation but induce angiogenesis in vivo" Tissue Engineering 2013, vol. 19, No. 13-14, pp. 1641-1653.

Radia Tamarat "Anthos project", 1er mars 2015, p. 1.

Mammoto, T., et al., "Platetet rich plasma extract promotes angiogenesis through the angiopoietin1-Tie2 pathway," Microvascular Research 2013;89:15-24.

Tong, M., et al., "Diabetes-Impaired Wound Healing Is Improved By Matrix Therapy With Heparan Sulfate Glycosaminoglycan Mimetic OTR4120 in Rats," Diabetes 2012, vol. 61, No. 10, pp. 2633-2641.

(56) References Cited

OTHER PUBLICATIONS

Ito, R., et al., "Efficacy of the Controlled Release of Concentrated Platelet Lysate from a Collagen/Gelatin Scaffold for Dermis-Like Tissue Regeneration," Tissue Engineering Part A 2013, vol. 19, No. 11-12, pp. 1398-1405.
Lafont, J., et al., "Kinetic Study of Early Regenerative Effects of RGTA11, a Heparin Sulfate Mimetic, in Rat Craniotomy Defects," Calcified Tissue International 2004, Springer-Verlag, vol. 75, No. 6, pp. 517-525.
Meddahi, A., et al., "New concepts in tissue repair: skin as an example,"Diabetes & Metabolism 1996, vol. 22, No. 4, pp. 274-278.
Dash, N. R., et al., "Targeting Nonhealing Ulcers of Lower Extremity in Human Through Autologous Bone Marrow-Derived Mesenchymal Stem Cells," Rejuvenation Research 2009;12(5):359-366.
Tong, M., et al., "RGTA OTR 4120, a heparan sulfate proteoglycan mimetic, increases wound breaking strength and vasodilatory capability in healing rat full-thickness excisional wounds," Diabetes 2016;61:2633-2641.
"A Lesion . . . What Does the Doctor Mean?" https://www.medicinenet.com/script/main/art.asp?articleket=9695, downloaded Oct. 22, 2018, 2 pages.
Sutton, A., et al., "Glycosaminoglycan and their synthetic mimetics inhibits RANTES-induced migration and invasion of human hepatoma cells," Molecular Cancer Therapeutics 2017, vol. 6, No. 11, pp. 2948-2958.
Frescaline, G., et al., "Glycosaminoglycans mimetics potentiate the clonogenicity, proliferation, migration and differentiation properties of rat mesenchymal stem cells," Stem Cell Research 2011, vol. 8, No. 2, pp. 180-192.
International Search Report and Written Opinion for PCT Patent App. No. PCT/EP2016/061906 (dated Sep. 5, 2016).
Search Report from European Patent App. No. 15305807.8 (dated Oct. 13, 2015).
Extended Search Report from European Patent App. No. 15305807.8 (dated Jan. 12, 2016).
Petit, E. et al., "Controlled Sulfatation of Natural Anionic Bacterial Polysaccharides Can Yield Agents with Specific Regenerating Activity in Vivo," Biomacromolecules Mar.-Apr. 2004; 5(2):445-452.
A. Sutton, et al., "Glycosaminoglycans and their synthetic mimetics inhibit RANTES-induced migration and invasion of human hepatoma cells", Molecular Cancer Therapeutics, vol. 6, No. 11, 2007, pp. 2948-2958.
G. Frescaline, et al., "Glycosaminoglycans mimetics potentiate the clonogenicity, proliferation, migration and differentiation properties of rat mesenchymal stem cells", Stem Cell Research, Elsevier, vol. 8, 2012, pp. 180-192.
Moussa L, Demarquay C., et al. "Heparan Sulfate Mimetics: A New Way to Optimize Therapeutic Effects of Hydrogel-Embedded Mesenchymal Stromal Cells in Colonic Radiation-Induced Damage," Sci Rep. Jan. 17, 2019;9(1):164. doi: 10.1038/s41598-018-36631-6.
Jennifer Schulze, et al. "Microenvironmental support for cell delivery to the inner ear," Hearing Research 368 (2018) 109e.
Tong, M., et al., "RGTA OTR 4120, a heparan sulfate proteoglycan mimetic, increases wound breaking strength and vasodilatory capability in healing rat full-thickness excisional wounds" Wound Repair and Regeneration, 16: pp. 294-299 (Mar. 4, 2008).
Garcia-Filipe S., et al., "RGTA OTR4120, a heparan sulfate mimetic, is a possible long-term active agent to heal burned skin" Journal of Biomedical Materials Research. Part A, 80(1): pp. 75-84 (Jan. 2007).
Zakine G., et al., "Matrix therapy with RGTA OTR4120 improves healing time and quality in hairless rats with deep second-degree burns"; Plastic and Reconstructive Surgery, 127(2): pp. 541-550 (Feb. 2011).
Deirdre R. Coombe et al., "Heparin Mimetics," Handbook of Experimental Pharmacology, 2012, vol. 207, pp. 361-383.

\* cited by examiner

COMPOSITION FOR TREATING TISSUE LESIONS

CROSS REFERENCE TO RELATED APPLICATIONS

This application is a national phase filing under 35 C.F.R. § 371 of and claims priority to PCT Patent Application No. PCT/EP2016/061906, filed on May 26, 2016, which claims the priority benefit under 35 U.S.C. § 119 of European Patent Application Nos. 15305807.8, filed May 28, 2015, the contents of each of which are hereby incorporated in their entireties by reference.

BACKGROUND

Some embodiments relate to a pharmaceutical composition for use as a medicament for the prevention and/or treatment of tissue lesions.

Some embodiments also relate to a pharmaceutical kit for the prevention and/or treatment of tissue lesions.

Some embodiments also relate to the use of a pharmaceutical composition for producing a medicament for the treatment of tissue lesions.

Some embodiments can be used in particular in the pharmaceutical and veterinary fields.

In the description below, the references between parentheses ( ) refer back to the list of references presented at the end of the text.

RELATED ART

The implantation of cells, of tissues or of organs for therapeutic purposes is a major challenge in medicine. Many studies, spread over close to a century, have demonstrated the therapeutic benefits of these implantations in many applications and numerous techniques have made it possible to control and improve the quality of the specimens, the storage and preservation thereof, or the expansion thereof before implanting them or reintroducing them into the recipient patient. Likewise, numerous improvements have been made to the performance levels and properties of the organs, tissues or cells that are used in methods, devices and products for the purpose of providing the recipient patient with a therapeutic benefit after reintroduction. Finally, better knowledge and control of the adverse reactions sometimes associated with this reintroduction has also made it possible to ensure better success.

However, after administration of the cells, the yields regarding their integration and/or the therapeutic efficiency given the number of cells administered remains very low, thus involving the need to repeat the treatment and very high treatment costs. In addition, the low yields and high costs limit the pathological conditions and/or the patients capable of being treated by way of these methods.

There is therefore a real need in the related art to be able to further improve these methods and/or the biological tools used in order to optimize their use and to be able to broaden the therapeutic field of application.

There are in the related art compounds that are capable of improving the tissue environment, for example polymers known as HBGFPPs for "Heparan Binding Growth Factor Protectors and Potentiators). These HBGFPPs were defined by their property of protecting growth factors that have affinity for heparin (such as FGF, TGFb and the like) against degradations by proteases and also for potentiating the activity of these factors without exhibiting any significant anticoagulant activity at the doses used. These HBGFPPs exhibited surprising properties on the repair of muscle tissue, nerve tissue and digestive tract tissue lesions and also an activity on the inflammatory reaction, as illustrated in particular by International application WO 1995/026739 or in American patent U.S. Pat. No. 7,998,922. These polymers were also defined chemically and illustrated as tissue regeneration agents in preclinical models of cutaneous, bone, cornea and ischemic tissue lesions. They also demonstrated antifibrotic effects, single capacities for protection against the effects of oxidative stress in ischemia models, protective effects against aging and neurodegeneration and, in general, they promote regeneration processes. One particular form of HBGFPP, the RGTAs, demonstrated, during use thereof, an acceleration and improvement in the repair of tissue lesions, for instance skin, cornea, bone or else muscle; and possibly a decrease in scar traces and more generally in fibroses (see review Van Neck et al., Heparan Sulfate Proteoglycan Mimetics Promote Tissue Regeneration: An Overview chapter 4 in Tissue Regeneration—From Basic Biology to Clinical Application ISBN 978-953-51-0387-5, edited by Jamie Davies). RGTAs are also known to be able to protect against harmful effects caused by irradiation—(Mangoni M et al.; Int. J. Radiation Oncology Biol. Phys. 2009,74, 1242-1250), by oxidative stress in the case of lesions caused by irradiation (Yue X-L et al.; Cell Death and Differentiation 2009, 1-12), by oxidative stress during ischemia (Desgranges et al.; FASEB J. 1999 Apr.; 13(6):761-6) or also in the case of tissue aging (Larramendy-Gozalo C, D et al.; J Gen Virol. 2007, 88:1062-7).

In another therapeutic field, other effects of RGTAs have also been observed, in particular in the treatment of pain and of itching and for which those with ordinary skill in the art could not foresee a link with the tissue repair or regeneration process since the effect was very rapid and therefore independent of the repair or regeneration process which takes much longer to perform.

RGTAs have been described and used for repairing lesioned tissues via in particular the protection of growth factors and of cell communications present on the lesion site and also the recruitment of the cells that exist in the treated patient. For example, publications have shown an effect of RGTAs on the mobilization of endogenous stem cells such as hematopoietic progenitor cells, or blood-derived stem cells (Albanes et al., Experimental Hematology 2009;37: 1072-1083) or on the growth, clonogenicity, migration and/or differentiation of mesenchymal stem cells in vitro or in vivo.

The use of RGTAs including benzylamine with bone marrow cells has been envisioned in International application WO 2003/101201 for the treatment of myocardial infarction for increasing the formation of collateral blood vessel vascularization. However, this disclosure includes no experiments, nor any scientific results. Thus, the elements included in the document do not make it possible to reproduce the elements described or to envision any treatment. In particular, the document Mullanghi et al. (Coronary; 22: 71) reports that RGTA coinjected with mesenchymal cells taken on the same day from bone marrow and directly injected into the infarcted area after ligature of the descending coronary artery in baboons does not have more functional efficiency than the RGTA injected alone into this muscle, thus reproducing the observations of Yamauchi H et al., FASEB J. 2000 (14): 2133-4, which show that the RGTA alone had a strong capacity to improve post-infarction recovery of the myocardium. The coinjection of the cells and of the RGTA therefore provides no additional beneficial effect regarding post-infarction recovery of the myocardium compared with the use of RGTA alone. In other words, no additional beneficial effect has been observed/demonstrated when injecting cells and RGTAs.

The literature also refers to numerous cell therapy studies aimed at implanting, by various methods, cells of different origin and different nature in order to recolonize areas of lesioned tissues or of tissues with impaired functions. From all or most these studies, it emerges that it is extremely difficult to obtain survival of the cells implanted in the targeted area, and even more difficult to obtain a colonization of the space and even more so a recovery over time of the functions of the organ or of the tissue having thus been recolonized. This problem remains a real challenge that has not yet been satisfactorily overcome.

There is therefore a real need to find a novel compound and/or method capable of improving the treatment of tissue lesions and/or the efficiency of cell therapies.

The use of RGTA mixed with a bone substitute biomaterial is described in the related art (Billy et al., patent US 2006/0257449). The document also envisions combining this (tricalcium) biomaterial with stem cells, not RGTAs, for trying to promote the implantation and colonization of the bone substitute, but it gives no explanation or description with regard to a possible implementation, step etc. In addition, this disclosure includes no experiments, nor any scientific results. Thus, the elements described in the document and the teaching thereof do not enable the reproduction or the development of any combination of a bone substitute biomaterial and cells, or any use of any combination.

Numerous pathological conditions, in particular caused by aging, include tissue and/or cell degeneration phenomena, for example Alzheimer's disease, macular degeneration, and/or caused by biological phenomena such as a decrease in the oxygenation of tissues/cells, etc.

For these pathological conditions, and as mentioned above, there is a great need in the related art to find effective treatments, and/or in particular to improve existing treatments, in particular regarding cell therapies.

There are also numerous genetic pathological conditions involving in particular poor tissue and/or cell function for which the treatments are virtually nonexistent or not very effective. For these pathological conditions, one treatment route can include or can consist of cell therapy. However, the efficiency of these therapies is questioned, in particular because of the weak cell implantation after injection and/or the very high costs of these treatments.

There is therefore a real need to find a novel composition and treatment making it possible to treat tissue lesions regardless of their origin and/or to increase the treatment efficiency of the known compositions and/or the cell therapies while at the same time reducing their cost.

SUMMARY

The object of some embodiments is specifically to meet these needs by providing a pharmaceutical composition for use as a medicament for the prevention and/or treatment of tissue lesions, the composition including:

a biocompatible polymer of general formula (I) below $$AaXxYy \qquad (I)$$

in which:
A represents a monomer,
X represents a —$R_1COOR_2$ or —$R_9(C=O)R_{10}$ group;

Y represents an O- or N-sulfonate group which corresponds to one of the following formulae —$R_3OSO_3R_4$, —$R_5NSO_3R_6$, —$R_7SO_3R_8$, in which:
$R_1$, $R_3$, $R_5$ and $R_9$ independently represent an aliphatic hydrocarbon-based chain which is optionally branched and/or unsaturated and which optionally contains one or more aromatic rings, $R_2$, $R_4$, $R_6$ and $R_8$ independently represent a hydrogen atom or a cation, $R_7$ and $R_{10}$ independently represent a bond, or an aliphatic hydrocarbon-based chain which is optionally branched and/or unsaturated, "a" represents the number of monomers,
"x" represents the degree of substitution of the monomers A by groups X,
"y" represents the degree of substitution of the monomers A by groups Y, and
a eukaryotic cell.

Advantageously, the presently disclosed subject matter demonstrates, surprisingly and contrary to the teachings of the related art, that the combination of biocompatible polymers of general formula (I) as defined above, also denoted RGTA in the present document, and of cells makes it possible both to prepare or condition the tissues and organs, for example of the recipient patient, and to promote the implantation, the expansion and the colonization of the external cells and/or of organ and/or tissue transplants, for example in the recipient patient.

In particular, the presently disclosed subject matter demonstrates, surprisingly, that the use of biocompatible polymers of general formula (I) combined with cells, organs, platelet extracts advantageously and surprisingly makes it possible to notably improve the recovery of the impaired functions of the tissues and/or organs thus treated, to the great benefit of the patient.

In addition, the presently disclosed subject matter demonstrates that the combination of biocompatible polymers of general formula (I) with cells according to some embodiments can used/applied for a large number of pathological conditions/lesions, etc. Indeed, some embodiments can be applied regardless of the lesioned/implanted or grafted tissues or organs, regardless of the cells that are used, for example injected, for example alone or in combination for example with platelet lysates, for example enriched with growth factors or for example with injection of purified growth factors, in particular growth factors which have an affinity for RGTAs or for heparan sulfates.

The presently disclosed subject matter also demonstrates, surprisingly, that the effect obtained on the functional recovery of the tissue treated is greater than the effect obtained separately either by the RGTA alone or by the cells alone or by the tissue or the organ or the biomaterial or platelet lysates or pure growth factors implanted or injected alone.

The presently disclose subject matter also demonstrates, surprisingly and unexpectedly, that the dosage regimen, therapeutic scheme for administration of the composition, advantageously makes it possible to optimize the therapeutic effects and also has a strong synergistic effect observed in the functional and healing recovery of the tissues or organs treated.

The results observed are all the more unexpected since the cells used according to some embodiments can have properties and origins that are different than those of the cells present in the tissues or organs in which they may be implanted. Surprisingly, the composition according to some embodiments promote the colonization of the implanted cells to the extent, for example, that a tissue or organ that is again functional is observed, despite the fact that these implanted cells may be of a different phenotype and of a different tissue origin. In addition, this is without having to experimentally induce the emergence of pluripotent stem cells or stem cells that are already committed to the differentiation pathway of the cells of the tissue or organ to be colonized.

The presently disclosed subject matter demonstrates, surprisingly, that the use of the RGTA according to some embodiments make it possible to obtain a new and unexpected technical/therapeutic effect, namely in particular a conditioning of the lesion site by preparing the implantation area, and to obtain a greater implantation of the cells/efficacy of the therapeutic treatment than that obtained when the RGTA is used alone and/or than that of the cells used alone, in particular regarding the efficiency of the cell treatment and/or the implantation capacity of the cells or tissues or organs.

Thus, the presently disclosed subject matter demonstrates, surprisingly and unexpectedly, that some embodiments, via for example the sequential administration, that is to say according to a dosage regimen, of RGTA followed, after a certain period of time ranging, for example, from a few minutes to a few days, by the administration of cells of any nature and/or origin that have been chosen, advantageously makes it possible to promote, unexpectedly, the engraftment of these transplants or the functional implantation of these cells regardless of the origin, their state of development and the method of preparation, provided that, where appropriate, the rejection aspects associated with the recipient's immune system are controlled.

In addition, the presently disclosed subject matter demonstrates, in particular in the examples, that some embodiments can be applied to, and in particular the lesions capable of being treated by the composition according to some embodiments can be, any type of tissue lesion regardless of the origin and also any type of tissue or organ. In particular, those with ordinary skill in the art, in the light of the examples below in which a great diversity of lesions are effectively treated, easily understands, and can, in the light of this knowledge extrapolate to, the other tissue lesions capable of being treated by some embodiments.

In the present document, the term "tissue lesions" is intended to mean any lesion of any biological tissue of a mammal that is known to those with ordinary skill in the art. It may for example be a connective tissue, muscle tissue, nervous tissue, bone tissue, cartilage tissue and/or epithelial tissue lesion. It may for example be any lesion of any mammalian organs or organelle known to those with ordinary skill in the art. It may for example be a lesion of the tissues of the digestive tract, of the tissues of the gastrointestinal tract, of the digestive alimentary and excretion system, of the genital tract, of the reproductive system, of the optic, olfactory or auditive system, of the sensory system, of the circulatory and/or cardiovascular system, of the respiratory system, of the muscle system or of the locomotive system. It may for example be a lesion of the gastric tissue, a buccal lesion, a lesion of the cornea, a tympanic lesion, a cochlear lesion, a skin lesion, for example a wound, a chronic wound, for example a diabetic wound, an ulcerative wound, a pressure sore, a skin burn, a necrotizing wound, a venous lesion, an ischemic lesion, for example an ischemic necrosis, a lesion caused by an infarction, for example a myocardial infarction, a bone lesion, for example a fracture, a fracture with bone defect, an osteonecrosis ("non union bone fracture"), an osteochondral lesion, a cartilage lesion, a tendon lesion, a surgical lesion, a lesion caused by a surgical procedure, a lesion caused by a medical treatment, for example radiotherapy, a nervous tissue lesion, for example a brain lesion, for example a lesion caused by exeresis of a tumor, a spinal cord lesion, a nerve fiber lesion, for example a locomotor and/or sensory system lesion, a respiratory system lesion, for example pulmonary lesions, a circulatory system lesion, for example a lesion of the arteries and/or of the vessels, a lesion of the digestive, renal, urinary system.

In the present document, the term monomer is intended to mean for example a monomer chosen from the group including sugars, esters, alcohols, amino acids or nucleotides.

In the present document, the monomers A constituting the basic elements of the polymers of formula I may be identical or different.

In the present document, the linking of monomers can make it possible to form a polymer backbone, for example a polymer backbone of polyester, polyalcohol or polysaccharide nature, or of nucleic acid or protein type.

In the present document, among the polyesters, they may for example be biosynthetic or chemically synthesized copolymers, for example aliphatic polyesters or polyesters of natural origin, for example polyhydroxyalkanoates.

In the present document, the polysaccharides and derivatives thereof may be of bacterial, animal, fungal and/or plant origin. They may for example be single-chain polysaccharides, for example polyglucoses, for example dextran, cellulose, beta-glucan, or other monomers including more complex units, for example xanthans, for example glucose, mannose and glucuronic acid, or else glucuronans and glucoglucuronan.

In the present document, the polysaccharides of plant origin may be single-chain, for example cellulose (glucose), pectins (galacturonic acid), fucans, or starch, or may be more complex, for instance alginates (galuronic and mannuronic acid).

In the present document, the polysaccharides of fungal origin may for example be steroglucan.

In the present document, the polysaccharides of animal origin may for example be chitins or chitosan (glucosamine).

The number of monomers A defined in formula (I) by "a" may be such that the weight of the polymers of formula (I) is greater than approximately 2000 daltons (which corresponds to 10 glucose monomers). The number of monomers A defined in formula (I) by "a" may be such that the weight of the polymers of formula (I) is less than approximately 2 000 000 daltons (which corresponds to 10 000 glucose monomers). Advantageously, the weight of the polymers of formula (I) may be from 2 to 100 kdaltons.

In the present document, in the —$R_1COOR_2$ group representing X, $R_1$ may be a $C_1$ to $C_6$ alkyl, for example a methyl, an ethyl, a butyl, a propyl or a pentyl, preferably a methyl group, and $R_2$ may be a bond, a $C_1$ to $C_6$ alkyl, for example a methyl, an ethyl, a butyl, a propyl or a pentyl, or an $R_{21}R_{22}$ group in which $R_{21}$ is an anion and $R_{22}$ a cation chosen from the group of alkali metals.

Preferably, the group X is the group of formula —$R_1COOR_2$ in which $R_1$ is a methyl group —$CH_2$— and $R_2$ is a $R_{21}R_{22}$ group in which $R_{21}$ is an anion and $R_{22}$ a cation chosen from the group of alkali metals, preferably the group X is a group of formula —$CH_2$—$COO^-$.

In the present document, in the —$R_9(C=O)R_{10}$ group representing X, $R_9$ may be a $C_1$ to $C_6$ alkyl, for example a methyl, an ethyl, a butyl, a propyl or a pentyl, preferably a methyl group, and $R_{10}$ may be a bond, or a $C_1$ to $C_6$ alkyl, for example a methyl, an ethyl, a butyl, a propyl, a pentyl or a hexyl.

In the present document, in the group corresponding to one of the following formulae —$R_3OSO_3R_4$, —$R_5NSO_3R_6$ and —$R_7SO_3R_8$ and representing the group Y, $R_3$ may be a bond, a $C_1$ to $C_6$ alkyl, preferably a methyl, an ethyl, a butyl, a propyl or a pentyl, for example a methyl group, $R_5$ may be a bond, a $C_1$ to $C_6$ alkyl, for example a methyl, an ethyl, a butyl, a propyl or a pentyl, preferably a methyl group, $R_7$ may be a bond, a $C_1$ to $C_6$ alkyl, for example a methyl, an ethyl, a butyl, a propyl or a pentyl, preferably a methyl group, and $R_4$, $R_6$ and $R_8$ may independently be a hydrogen atom or a cation $M^+$, for example $M^+$ may be an alkali metal.

Preferably, the group Y is the group of formula —$R_7SO_3R_8$ in which $R_7$ is a bond and $R_8$ is an alkali metal chosen from the group including lithium, sodium, potassium, rubidium and cesium. Preferably, the group Y is an —$SO_3^-Na^+$ group.

The degree of substitution of all of the monomers A by the groups Y defined in general formula (I) by "y" may be from 30% to 150%, and preferably about 100%.

In the present document, in the definition of the degrees of substitution above, the term "a degree of substitution "x" of 100%", is intended to mean the fact that each monomer A of the polymer of some embodiments statistically contains a group X. Likewise, the term "a degree of substitution of "y" of 100%" is intended to mean the fact that each monomer of the polymer of some embodiments statistically contains a group Y. The degrees of substitution greater than 100% reflect the fact that each monomer statistically bears more than one group of the type in question; conversely, the degrees of substitution of less than 100% reflect the fact that each monomer statistically bears less than one group of the type in question.

The polymers may also include functional chemical groups, denoted Z, different than X and Y.

In the present document, the groups Z may be identical or different, and may independently be chosen from the group including amino acids, fatty acids, fatty alcohols, ceramides, or derivatives thereof, or targeting nucleotide sequences.

The groups Z may also represent active agents, which may be identical or different. They may for example be therapeutic agents, diagnostic agents, an anti-inflammatory, an antimicrobial, an antibiotic, a growth factor, an enzyme.

In the present document, the group Z may advantageously be a saturated or unsaturated fatty acid. It may for example be a fatty acid chosen from the group including acetic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, trans-vaccenic acid, linoleic acid, linolelaidic acid, α-linolenic acid, γ-linolenic acid, dihomo-γ-linolenic acid, arachidonic acid, eicosapentaenoic acid, clupanodonic acid or docosahexaenoic acid. Preferably, the fatty acid is acetic acid.

In the present document, the group Z may advantageously be an amino acid of the L or D series chosen from the group including alanine, asparagine, an aromatic chain, for example tyrosine, phenylalanine, tryptophan, thyroxine or histidine.

Advantageously, the groups Z may confer additional biological or physicochemical properties on the polymers. For example, the groups Z may increase the solubility or the lipophilicity of the polymer, enabling for example better tissue diffusion or penetration.

The polymers in which Z is present correspond to formula II below:

$$A_a X_x Y_y Z_z$$

in which A, X, Y, a, x and y are as defined above and z represents the degree of substitution by groups Z.

In the present document, the degree of substitution by groups Z represented by "z" may be from 0 to 50%, preferably equal to 30%.

The groups X, Y and Z may independently be bonded to the monomer A and/or independently bonded to one another. When at least one of the groups X, Y and Z is independently bonded to a group X, Y and Z different than the first, one of the groups X, Y or Z is bonded to the monomer A.

Thus, the groups Z may be directly covalently bonded to the monomers A or covalently bonded to the groups X and/or Y.

In the present document, the composition may include a concentration of 0.01 microgram to 100 mg by weight of biocompatible polymer relative to the total weight of the composition. For example, the composition may include from 10 micrograms to 10 milligrams by weight relative to the total weight of the composition.

In the present document, the composition may be formulated and/or adapted according to its administration. For example, for intravenous or intramuscular administration, the composition may be administered in order to deliver a dose of biocompatible polymer of from 0.1 to 5 mg per kilogram of body weight, or for oral administration, the composition may be administered, for example in 2 to 5 equal intakes per day, in an amount of a daily total for example of from 1 to 500 mg, for example 10 microg to 5 mg per kg of biocompatible polymer, for example from 10 microg to 5 mg per kg, for example for an adult with a body weight of 100 kg, for several days to several weeks. For example, for intracranial administration, it may involve a single administration of from 1 to 5 ml, or an administration by mini pump over the course of several days; the composition may include a concentration of from 0.001 to 1 $mg.ml^{-1}$ of biocompatible polymer, or for a sublingual administration, for example daily from 1 to 5 ml, the composition may include a concentration of from 0.1 to 100 $mg.ml^{-1}$ of biocompatible polymer, or for areal administration, the composition may be administered in order to deliver a dose of from 0.1 to 5 mg of biocompatible polymer per kilogram of body weight of the polymer.

For example, for oral administration, the polymer may be in solution, for example in water or in any solvent suitable for oral administration known to those with ordinary skill in the art. The composition may also be in the form of a tablet, a gel capsule or any other form compatible with oral intake known to those with ordinary skill in the art. It may be an aqueous solution having a volume of from 10 to 50 ml including for example a concentration of 0.1 $mg.ml^{-1}$ of polymer in the solution. For example, for systemic administration, the polymer may for example be in solution in physiological saline, for example physiological saline of injectable quality or any other form compatible with injection, for example solutions with glucose and/or other suitable excipients known to those with ordinary skill in the art, for example including polysaccharides, for example heparin. For example, the polymer may be at a concentration of from 0.1 to 5 $mg.kg^{-1}$, preferably from 1 to 2.5 $mg.kg^{-1}$, for example for intravenous (IV) and/or intramuscular (IM) administration.

According to some embodiments, the composition may also include growth factors. They may be any growth factor known to those with ordinary skill in the art that is capable of promoting or stimulating cell growth. They may for example be growth factors chosen from the group including fibroblast growth factor (FGF), for example FGF1 or FGF2, vascular endothelial growth factor (VEGF), platelet-derived growth factor (PDGF) or a mixture thereof. According to some embodiments, the composition may include from 10 nanog.ml$^{-1}$ to 100 microg.ml$^{-1}$ of growth factors.

According to some embodiments, the composition may also include a crude or growth factor-enriched platelet extract or lysate. It may for example be any platelet extract or lysate that is known to those with ordinary skill in the art and/or commercially available.

In the present document, the term "eukaryotic cell" is intended to mean any eukaryotic cell known to those with ordinary skill in the art. It may for example be a mammalian eukaryotic cell, for example an animal or human eukaryotic cell. It may for example be any eukaryotic cell regardless of its differentiation stage, for example a cell chosen from the group including adult or embryonic eukaryotic cells, embryonic stem cells and adult stem cells. They may for example be eukaryotic cells from umbilical cord blood, from bone marrow cells, from adipose tissue cells, from mesenchymal cells. They may also be a group of cells, from a graft and/or from an organ.

The eukaryotic cell may for example be a cell that is heterologous, homologous or autologous with respect to an individual. Preferably, the cells are autologous cells.

It may also be a pluripotent or totipotent stem cell, or cells committed to differentiation pathways, for example mesenchymal stem cells. It may also be a pluripotent or totipotent stem cell with the exception of embryonic stem cells.

Advantageously, when the cells are autologous, the composition according to some embodiments may be preferred for regulatory, safety, feasibility, efficiency and economic reasons.

Advantageously, when the cells are autologous, they are preferably isolated from the individual and used in the composition according to some embodiments and/or used in a treatment within 24 hours after removal and isolation without other additions. Advantageously, this single administration makes it possible to overcome and to conform to the regulatory requirements/restrictions.

In the present document, the amount of cells included in the composition may be from 1 to $5 \times 10^7$ cells.

Advantageously, the presently disclosed subject matter demonstrates that the treatment is independent of the cell type, of its origin, and of the way used to select, amplify, condition and modify the cells. In particular, the presently disclosed subject matter demonstrates, surprisingly, that some embodiments thus applies to all cells regardless of their origins and the selection manipulations resulting in committing the cells to differentiation or dedifferentiation pathways in so far as the administration of the RGTA advantageously makes it possible, in particular when it is combined with the administration of cells, to create/form a microenvironment suitable for the cell, advantageously enabling a synergistic cooperation between the RGTA and the cells, making it possible to increase the cell implantation.

According to some embodiments, when the composition includes a graft or a transplant organ, or an implantable material, the administration of the polymer and of the graft or organ or of the implantable material may be simultaneous. For example, the organ to be transplanted or the implantable material may be impregnated, for example either by immersing it in a solution including the biopolymer, or by perfusion, or by spraying or any other suitable method known to those with ordinary skill in the art. In the case of implantable material, the polymer may be incorporated as early as the manufacture of the implantable material, advantageously enabling a preincubation or impregnation.

According to some embodiments, the impregnation time may be from a few minutes to several hours, for example from 1 minute to 18 hours, from 5 minutes to 16 hours, overnight.

Advantageously, when the graft or organ is impregnated for a time greater than 5 minutes, for example of 16 hours, the impregnation also makes it possible to improve the efficiency of transplant engraftment. This is because the inventors have shown, surprisingly, that the presence of the polymer in the solution for preserving the graft and/or the organ advantageously has a protective and anti-apoptotic effect.

Advantageously, the graft, the organ or the material impregnated with the polymer may receive, before or after the reimplantation or the transplantation, an administration of growth factors or of platelet extract in order to promote the colonization by the cells administered at the time of the implantation or afterwards.

In the present document, the term "pharmaceutical composition" is intended to mean any form of pharmaceutical composition known to those with ordinary skill in the art. In the present document, the pharmaceutical composition may for example be an injectable solution, for example for a local or systemic injection, for example in a physiological saline, in an injectable glucose solution, in the presence of excipients, for example of dextrans, for example at concentrations known to those with ordinary skill in the art, for example from one microgram to a few milligrams per ml.

The pharmaceutical composition may for example be a medicament intended for oral administration, chosen from the group including a liquid formulation, an oral effervescent dosage-regimen form, an oral powder, a multiparticle system, and an orodispersible galenic form.

For example, when the pharmaceutical composition is for oral administration, it may be in the form of a liquid formulation chosen from the group including a solution, a syrup, a suspension and an emulsion. When the pharmaceutical composition is in the form of an oral effervescent dosage-regimen form, it may be in a form chosen from the group including tablets, granules and powders. When the pharmaceutical composition is in the form of an oral powder or a multiparticulate system, it may be in a form chosen from the group including beads, granules, mini tablets and microgranules. When the pharmaceutical composition is in the form of an orodispersible dosage-regimen form, it may be in a form chosen from the group including orodispersible tablets, lyophilized wafers, thin films, a chewable tablet, a tablet, a capsule or a medical chewing gum.

According to some embodiments, the pharmaceutical composition may be a pharmaceutical composition for oral administration, for example buccal and/or sublingual administration, for example chosen from the group including buccal or sublingual tablets, lozenges, drops and a spray solution.

According to some embodiments, the pharmaceutical composition may be a pharmaceutical composition for topical, transdermal administration, for example chosen from the group including ointments, creams, gels, lotions, patches and foams.

According to some embodiments, the pharmaceutical composition may be a pharmaceutical composition for nasal administration, for example chosen from the group including nasal drops, a nasal spray and nasal powder.

According to some embodiments, the pharmaceutical composition may be a pharmaceutical composition for parenteral administration, for example subcutaneous, intramuscular, intravenous or intrathecal administration.

The composition of some embodiments may also include at least one other active ingredient, particularly another therapeutically active ingredient, for example for simultaneous, separate or sequential use over time, according to the galenic formulation used. This other ingredient may for example be an active ingredient used for example in the treatment of opportunistic diseases that can develop in a patient with a tissue lesion.

In the present document, the administration of the biocompatible polymer and of the cell may be simultaneous, successive or concomitant.

According to some embodiments, at least one of the administrations may be carried out orally or by injection. The two administrations can be carried out in the same way or differently. For example, the administration of the biocompatible polymer and of the cells may be carried out by injection, the administration of the biocompatible polymer may be carried out orally and the cells may be by local injection. The administration may also depend on the site of the lesion.

According to some embodiments, the use of eukaryotic cells, in particular the administration thereof, may be carried out after a period of 5 minutes to 1 week following the first administration of the biocompatible polymer.

In the case of the transplantation of tissues or organs or the use of implantable materials pre-impregnated with the polymer, the administration of cells may be carried out before the implantation or just afterwards, for example within the hour.

According to some embodiments, the composition may for example be administered daily, twice daily or weekly. It may for example be an administration once a day, twice a day or more.

According to some embodiments, the composition may for example be administered over a period of 1 day to 3 months, for example for 2 months. For example, the composition may be administered over a period of 3 months with an administration frequency every 15 days.

According to some embodiments, the biopolymer may for example be administered over a period of 1 day to 3 months, for example for 2 months, with for example a frequency of once a day, and the eukaryotic cell administered may be administered over an identical or different period, for example a period from 1 day to 3 months, with a weekly frequency.

According to some embodiments, when the administration of the polymers and the administration of the cells are successive, the dosage regimen for each administration may be an administration of the polymers followed by the administration of the cells. For example, the cells may be administered from 1 minute to 24 hours after the administration of the polymers, from 30 minutes to 12 hours after administration of the polymers, from 45 minutes to 6 hours after administration of the polymers, or 1 hour after administration of the polymers.

According to some embodiments, the composition may also include a platelet extract. It may for example be any platelet extract known to those with ordinary skill in the art that is suitable for administration to a mammal. It may for example be a commercially available platelet extract, or a platelet extract obtained according to the process described in the document D R Knighton, et al., Ann Surg. September 1986; 204(3): 322-330 "Classification and treatment of chronic nonhealing wounds. Successful treatment with autologous platelet-derived wound healing factors (PD-WHF)" or in the documents Everts, P. A. M et al., Autologous platelet gel growth factor release and leukocyte kinetics using three devices. Transf. Med., 2006, 16(5), 363-368 or "Is Use of Autologous Platelet-Rich Plasma Gels in Gynecologic, Cardiac, and General, Reconstructive Surgery Beneficial?" Pharmaceutical Biotechnology, 2012, Vol. 13 No. 13). It may be a platelet extract corresponding to platelet lysates enriched with growth factor activity that can be administered for example locally, that can be injected or that can be deposited in varied supports, for example in or on gels, creams, sprays and/or in lesioned tissues. According to the some embodiments, the platelet extract may be an extract that is autologous or heterologous with respect to an individual to be treated. Preferably, the platelet extract is an autologous extract. It may for example be a platelet extract and/or lysate that has been concentrated, for example by processes and/or kits that are known to those with ordinary skill in the art and/or commercially available.

According to some embodiments, the composition may include from 0.1 ml to 100 ml of platelet extract and/or lysate.

Advantageously, the platelet extract includes growth factors which promote the formation of an "environment" conducive to the implantation of cells. These factors may be added to the platelet extract or used alone without extracts. According to some embodiments, the FGF1 or FGF2 or VEGF or TGFbeta1 or BMP factor or other growth factors, preferably at least one factor chosen from the group including the factor FGF1 or FGF2 or VEGF or TGFbeta1 or BMP, may be added. According to the some embodiments, the factors included in the platelet extract may be added at concentrations of from 10 ng to 100 microg/ml of extract.

According to some embodiments, prior to the administration of the composition, the lesioned tissue may be "reactivated" for example by re-opening the lesion, by scraping or by mechanical detersion with a scalpel. The reactivation may be carried out, for example, on old wounds, for example consolidated bone fractures, old scars or chronic wounds.

A subject of the presently disclosed subject matter is also a pharmaceutical or dermatological composition for use as a medicament for the prevention and/or treatment of tissue lesions, the composition including a biopolymer of formula AaXxYy or AaXxYyZz and at least one platelet extract.

According to the some embodiments, the platelet extract is as defined above.

According to some embodiments, the biopolymer of formula AaXxYy or AaXxYyZz is as defined above.

According to the some embodiments, the pharmaceutical or dermatological composition is as defined above.

According to some embodiments, the frequency of administration of the biocompatible polymer may be as defined above.

According to some embodiments, the method and/or the route of administration of the biocompatible polymer may be as defined above.

A subject of some embodiments is also a pharmaceutical or dermatological composition for use as a medicament for the prevention and/or treatment of tissue lesions, the composition including a biopolymer of formula AaXxYy or AaXxYyZz and at least one growth factor.

According to some embodiments, the growth factor is as defined above. According to some embodiments, the biopolymer of formula AaXxYy or AaXxYyZz is as defined above.

The pharmaceutical or dermatological composition is as defined above.

According to some embodiments, the frequency of administration of the biocompatible polymer may be as defined above.

According to some embodiments, the method and/or the route of administration of the biocompatible polymer may be as defined above.

Some embodiments also relate to a process for treating a patient having suffered a tissue lesion, including, in any order, the following steps:
i. the administration of at least one biocompatible polymer, and
ii. the administration of at least one eukaryotic cell, in which the administrations are concomitant, successive or alternating.

The biocompatible polymer is as defined above.
The eukaryotic cell is as defined above.

According to some embodiments, the patient may be any mammal. It may for example be an animal or a human being.

According to some embodiments, the eukaryotic cell administered may be a cell that is heterologous or homologous with respect to the patient.

According to some embodiments, the method and/or the route of administration of the biocompatible polymer may be as defined above.

According to the some embodiments, the method and/or the route of administration of the cell may be as defined above.

According to the some embodiments, the frequency of administration of the biocompatible polymer may be as defined above.

According to the some embodiments, the frequency of administration of the eukaryotic cell may be as defined above.

According to some embodiments, when the administration of the biocompatible polymers and the administration of the cells are successive, the dosage regimen for each administration may be an administration of the biocompatible polymers followed by the administration of the cells. For example, the cells may be administered from 1 minute to 48 hours after the administration of the biocompatible polymers, from 30 minutes to 12 hours after administration of the polymers, from 45 minutes to 6 hours after administration of the polymers, or 1 hour after administration of the polymers.

Advantageously, the eukaryotic cell is a mesenchymal adult stem cell.

Some embodiments also relate to a process for treating a patient having suffered a tissue lesion, including, in any order, the following steps:
i. the administration of at least one biocompatible polymer, and
ii. the administration of at least one platelet extract and/or lysate, in which the administrations are concomitant, successive or alternating.

The biocompatible polymer is as defined above.
The platelet extract and/or lysate is as defined above.

According to some embodiments, the patient may be any mammal. It may for example be an animal or a human being.

According to some embodiments, the method and/or the route of administration of the biocompatible polymer may be as defined above.

According to some embodiments, the frequency of administration of the biocompatible polymer may be as defined above.

According to some embodiments, when the administration of the biocompatible polymers and the administration of the platelet extract and/or lysate are successive, the dosage regimen for each administration may be an administration of the biocompatible polymers followed by the administration of the platelet extract and/or lysate. For example, the platelet extract and/or lysate may be administered immediately, that is to say concomitantly, or a few minutes, preferably from 10 minutes to a few hours, for example from 1 minute to 120 minutes, preferably from 10 to 60 minutes, after the administration, for example local administration, or an injection of the biocompatible polymers, after several hours, preferably from 4 h to 24 h, for example after oral administration of the biocompatible polymer.

Some embodiments also relate to a process for treating a patient having suffered a tissue lesion, including, in any order, the following steps:
i. the administration of at least one biocompatible polymer, and
ii. the administration of at least one growth factor,
in which the administrations are concomitant, successive or alternating.

The biocompatible polymer is as defined above.
The growth factor is as defined above.

According to some embodiments, the patient may be any mammal. It may for example be an animal or a human being.

According to some embodiments, the method and/or the route of administration of the biocompatible polymer may be as defined above.

According to some embodiments, the frequency of administration of the biocompatible polymer may be as defined above.

According to some embodiments, when the administration of the biocompatible polymers and the administration of the at least one growth factor are successive, the dosage regimen for each administration may be an administration of the biocompatible polymers followed by the administration of the at least one growth factor. For example, the at least one growth factor may be administered immediately, that is to say concomitantly, or for example from 1 minute to a few hours, for example from 1 minute to 120 minutes, preferably from 10 to 60 minutes, after the administration, for example local administration, or an injection of the biocompatible polymers, after several hours, preferably from 4 h to 24 h, after oral administration of the biocompatible polymer.

In other words, even though, in the present description, reference is made to a composition, it is clearly understood that each of the compounds of the composition may be administered concomitantly with the other compounds (for example in a single composition or in two compositions, each of these compositions including one or more of the abovementioned components, the method of administration of each of the compounds or composition(s) possibly being identical or different), or independently of one another, for example successively, for example independent administration of a biocompatible polymer and independent administration of a eukaryotic cell, these administrations being carried out on one and the same patient, concomitantly or successively or in an alternating manner, in an order which is that mentioned above or another order. These various administrations may be carried out independently of one another or in a linked manner (composition or co-administration), by an identical or different method of administration (injection, ingestion, topical application, etc.), one or more times a week, for one or more successive or non-successive weeks.

A subject of some embodiments is also a pharmaceutical kit for the prevention and/or treatment of tissue lesions including:

i. a biocompatible polymer, and
ii. at least one eukaryotic cell.

The biocompatible polymer is as defined above.

The eukaryotic cell is as defined above.

A subject of some embodiments is also a pharmaceutical kit for the prevention and/or treatment of tissue lesions including:
i. a biocompatible polymer, and
ii. at least one platelet extract and/or lysate.

The biocompatible polymer is as defined above.

The extract and/or lysate is as defined above.

A subject of some embodiments is also the use of a pharmaceutical composition including:
i. a biocompatible polymer, and
ii. at least one growth factor
for producing a medicament for the treatment of tissue lesions.

The biocompatible polymer is as defined above.

The growth factor is as defined above.

In this embodiment, the term "medicament" is intended to mean a pharmaceutical composition as defined above.

Advantageously, the presently disclosed subject matter demonstrates that the sequential administration of RGTA followed, after a certain period ranging from a few minutes to a few days, by cells, regardless of their natures and origins, advantageously and unexpectedly makes it possible to promote the functional implantation of the cells or the degree of the transplant engraftment. In addition, the presently disclosed subject matter also demonstrates that the abovementioned advantages have also been observed regardless of the origin, the developmental stage and/or the method of preparation of the cells used.

Advantageously, some embodiments therefore provide a general and simple answer to a complex technical problem and for which there is a real and persistent need in the related art. It is in particular illustrated in a nonlimiting manner in the examples below that, for those with ordinary skill in the art, can easily be extrapolated to any type of tissue lesion regardless of the origin and also to any type of tissue or organ.

In particular, the presently disclosed subject matter demonstrates that some embodiments can be generalized to all tissue lesions, in particular by virtue of certain common characteristics of tissue lesions, including destruction of cells and of the extracellular matrix at the level of the lesion site.

A subject of some embodiments is also an ex vivo process for preparing a transplant, including the impregnation of a graft and/or organ to be transplanted in a solution including a biocompatible polymer.

A subject of some embodiments is also the use of the biopolymer of formula AaXxYy or AaXxYyZz as defined above, for preparing, ex vivo, a graft and/or organ.

The biocompatible polymer is as defined above.

According to some embodiments, the impregnation can be carried out by any process known to those with ordinary skill in the art. It may for example involve immersing the organ and/or immersing it in a solution including the biopolymer, or perfusion, or spraying.

A subject of some embodiments is also the use of the biopolymer of formula AaXxYy or AaXxYyZz as defined above, for preparing, in vitro and/or ex vivo, an implantable biomaterial.

For example, for implantable biomaterials, the biocompatible polymer may be added, for example, by impregnation after production of the biomaterial, for example for a tissue or an organ. It may for example also be added during the production of the biomaterial from the start, for example the biopolymer of formula AaXxYy or AaXxYyZz as defined below may be added in successive layers, for example in a manner similar to 3D-printing.

In the present document, the term "implantable biomaterials" is intended to mean any implantable biomaterials that are known to those with ordinary skill in the art and/or commercially available. The implantable biomaterial may for example be a compatible implantable material, for example of any nature, which is biodegradable, crosslinked or non-crosslinked, preferably colonizable. The implantable biomaterials may be implantable biomaterials based on crosslinking of proteins, for example of collagens, of fibrin, of polysaccharides for example dextran, chitin, hyaluronic acid, alginate, cellulose and derivatives thereof, and biodegradable and biocompatible copolymers based on glycolic acid, lactic acid, or malic acid, or on polymers, that can for example take liquid-gel transitions by way of temperature-controllable polymerization, or by enzymes or irradiation or other processes. It may for example be a polymer based on polycaprolactone, polyurethane, polytetrafluoroethylene silicone, or based on inorganic salts, for example calcium phosphates or hydroxyapatites. The implantable biomaterials may for example be materials based on or made of ceramic, of metal, for example of aluminum, of steel, of titalen and/or of alloys thereof. Advantageously, when the material is a material based on or made of ceramic and/or of metal, the impregnation makes it possible to cover the external surface of the material; the impregnation may advantageously be carried out by spraying.

According to some embodiments, the impregnation solution may include a concentration of 0.1 microg.ml$^{-1}$ to 1 mg.ml$^{-1}$ of biocompatible polymer as defined above.

According to some embodiments, the impregnation time may be from 5 minutes to 24 hours. Advantageously, the impregnation time may depend on the structure of the implantable graft and/or organ and/or material.

Advantageously, the impregnation makes it possible also to improve the efficiency of transplant engraftment. Indeed, the inventors have shown, surprisingly, that the presence of the polymer in the solution for preserving the graft and/or the organ advantageously has a protective and anti-apoptotic effect.

The impregnation may advantageously be completed, after the impregnation with the biocompatible polymer, by an impregnation of growth factors and/or of platelet extracts, as mentioned above. According to the some embodiments, the growth factor and/or platelet extract impregnation time may be from 5 minutes to 24 hours.

The impregnation may advantageously be completed by ex vivo and/or in vitro impregnation and/or deposition of cells on the implantable biomaterial impregnated with the biocompatible polymer.

According to the some embodiments, the cells are as defined above.

According to some embodiments, the solution for impregnation and/or deposition of cells may include a concentration of a few thousand to a few million cells, preferably from 10 000 to 1 000 000 cells.

According to some embodiments, the time for ex vivo and/or in vitro impregnation and/or deposition of cells may be from 5 minutes to 24 hours.

In the present document, the impregnation and/or the deposition of cells on the implantable biomaterial impregnated with the biocompatible polymer may be carried out by any suitable process known to those with ordinary skill in the art.

In addition, according to some embodiments, the impregnation of implantable biomaterials may advantageously be completed, after the impregnation with the biocompatible polymer and/or ex vivo and/or in vitro impregnation or deposition of cells, by an impregnation of at least one growth factor.

According to some embodiments, the impregnation on the implantable biomaterial impregnated with at least one growth factor can be carried out by any suitable process known to those with ordinary skill in the art.

According to some embodiments, the growth factor is as defined above.

According to some embodiments, the solution for impregnation of at least one growth factor may include a concentration of 10 ng/ml to 100 microg/ml of growth factors.

According to some embodiments, the platelet extract and/or the platelet lysate is as defined above. It may for example be a concentrated platelet extract, for example from 5 to 100 ml of blood via, for example, the use of platelet concentration kits that are known to those with ordinary skill in the art and commercially available, for example the kits from Curasan (registered trademark), Plateltex (registered trademark), GPS (registered trademark) II and RegenLab (registered trademark).

According to some embodiments, the impregnation solution may include a concentration of 0.1 to 6 ml of platelet extract.

Other advantages may further emerge to those with ordinary skill in the art on reading the examples below, illustrated by the appended figures, and given byway of illustration.

EXAMPLES

Example 1

Preparation of RGTAs and Method of Administration

The RGTA synthesis is widely described in the related art, for example in the patent entitled—"PROCEDE DE SULFONATION DE COMPOSES COMPRENANT DES GROUPEMENTS HYDROXYLES (OH) LIBRES OU DES AMINES PRIMAIRES OU SECONDARES" ["PROCESS FOR SULFONATION OF COMPOUNDS INCLUDING FREE HYDROXYL (OH) GROUPS OR PRIMARY OR SECONDARY AMINES"] and also in the literature references: Yasunori I. et al., Biomaterials 2011, 32:769e776) and Petit E. et al. Biomacromolecules. 2004 March-April; 5(2):445-52.

In the examples below, several known and described RGTAs were used, of which OTR4120 (described in Khammari-Chebbi et al., J Fr Ophtalmol. 2008 May;31 (5):465-71) and OTR4131 (described in Frescaline G. et al., Tissue Eng Part A. 2013 Jul.;19(13-14):1641-53. doi: 10.1089/ten.TEA.2012.0377) which are commercially available. In addition, the compound OTR4131 is a compound including a Z radical which is a fatty acid, namely the acetic acid described in Virginie Coudry, et al. Long-Term Follow-up of Superficial Digital Flexor Tendonitis Treated by a Single Intralesional Injection of a ReGeneraTing Agent in 51 Horses Journal of Equine Veterinary Science 34 (2014) 1357-1360 and a compound in which Z is an amino acid such as phenylalanine, described in U.S. Pat. Nos. 7,998, 922, 8,790,631, were also used in the examples below.

In the examples below, the administration was carried out as described above. In other words, when the RGTA is not mixed in a single solution with the cells, the RGTA was administered according to the methods of administration known for this compound.

Advantageously, when the RGTA is administered via an independent composition, one of the effects obtained may be a preparation of the tissue or of the organ to be treated in order to promote an implantation, colonization and expansion by selected cells which allow a more efficient and synergistic tissue repair and regeneration by virtue of the combination of RGTA and cells.

The frequency of administration may be single or repeated every week or fifteen days or even monthly, rarely for a total period of several months, depending on the success of the colonization and the required number of injections/administrations of cells, the time required for the preparation of the niche before implantation.

The concentrations and doses of the RGTA that are administered depended on the local or systemic administration forms, on the frequencies, on the tissues, organs or areas to be treated, and on the volumes or surface area of the lesion.

In the examples below, when the administration is carried out orally, the RGTAs may be in solution in water or in the form of any other oral presentation form, but also in the form of a tablet, a gel capsule or any other form compatible with an oral intake. In addition, advantageously, the orally administered RGTAs exhibit a notable resistance to degradation by acid and by digestive juices. Advantageously, since the product has no taste and is completely soluble in water, the preferred intake is in the form of an aqueous solution in a volume of 10 to 25 ml and at a concentration of 0.1 mg.ml$^{-1}$ so that the amount is from 1 to 2.5 mg per intake, two to five times a day. In the majority of the examples, these intakes were in the morning before eating and in the evening at bedtime for patient weights ranging from 50 to 100 kg, the doses and frequencies possibly themselves also varying; thus, overall, the daily intake was between 1 and 500 mg/day. The period of this administration can be from several months without adverse effects having been observed. In particular, an intake by an individual of 25 mg/day over the course of more than one year induces no impairment nor any noticeable side effects.

In the case of treatment of the digestive tract with cells in order to repair and regenerate lesions, the amounts of RGTA can advantageously be reduced. This is because the RGTA molecules can advantageously reassemble directly with the lesioned tissue and, for example, recreate a niche, advantageously allowing better implantation of the cells and, where appropriate, making it possible to promote their proliferation. The doses used during treatment of the digestive tract may be, for example, from 1 to 50 ml at 100 microg.ml$^{-1}$ per day. They may for example be doses that are identical or similar to that described in the document Meddahi et al., J Biomed Mater Res 60: 497-501 2002, for example for the treatment of gastric or digestive ulcers, doses identical or similar to that described in the document Alexakis et al., Gut 2004;53:85-90 for the treatment of Crohn's diseases, or doses identical or similar to that described in the document Alexakis et al., FASEB J. 2001, 15,1546-1554 for tissues lesioned after irradiation.

In the examples below, when the administration is carried out by systemic injection, the RGTAs were preferably in solution in physiological saline of injectable quality or any other form compatible with injection, in particular solutions with glucose or other excipients that are usual with polysaccharides such as heparin, or mixed with therapeutic products having other properties, provided that the risk of interactions with other active ingredients has been evaluated. The RGTAs were used at concentrations of from 0.1 to 5 mg.kg$^{-1}$, preferably from 1 to 2.5 mg.ml$^{-1}$ intravenously (IV) or intramuscularly (IM). For this route of injection, the injection may be a single, daily or weekly injection.

In the examples below, when it was possible, the local administration in or in the vicinity of the lesioned tissue or site was preferred. In particular, this route of administration was preferred for the mucosae, for example buccal, vaginal, urethral, digestive mucosae with endoscopic vascular or cardiac access, and/or in areas where access is more difficult but can be directly reached, such as the bone marrow, the peri-retinal area, the intraventricular area, the pulmonary airways or else during surgery that opens up direct access or else directly through other tissues or organs with catheters, needles or suitable endoscopes.

The RGTA may also be administered as a spray on a tissue surface in the case of implantations of isolated cells or cells in sheets or else cells impregnated in implanted materials which are a support for existing or future cell colonization.

With regard to the airways, the administration may also be envisioned by inhalation.

With regard to the mucosae and/or the walls of the digestive tract or of the uterine muscles or of the ligaments, the rectal or vaginal route was preferred when accessible.

For the treatment of ocular tissues, the preferred administration form was, for example, in an eyewash, for example for the treatment of the cornea, by transcorneal injection for example in the treatment of the Descemet membrane, in the treatment of tissues covering the base of the eyeball, for example for the treatment of sight defects, or else for example for the treatment of a lesion of cells associated with hearing, for example for the implantation of cochlear ciliary cells.

In the examples, the local administration or injection may be single, daily or weekly, the dose then being related to the surface area or volume of the lesion. In particular, in the examples, the RGTA concentration was preferably 100 microg/ml which is the preferred concentration, and the volume used was chosen so as to cover the lesioned surface area or to impregnate the volume of the lesion. Thus, the perilesional injection into the tissue or the organ or into the site of 0.1 to 0.5 ml of RGTA made it possible to impregnate a tissue in a volume that was 5 to 100 times greater. In the surface application or application as a spray, where the RGTA penetrates by adsorption, the coverage of the lesioned area was sufficient. Thus, three to four "sprays" each of 140 ml at a distance of 5 cm from the lesion were sufficient to impregnate a surface area of 10 cm$^2$, alternatively a few milliliters of a cream or of a gel or ointment can be spread on the lesion or in the vicinity and thus provide access to the RGTA. The galenical forms of creams, ointments, gels, milks, foams, emulsions, powder pastes, etc. are those known to those with ordinary skill in the art and preferably chosen for their hydrophilic and moisturizing properties compatible with polysaccharides, for example hyaluronic acid.

In the examples, another method of administration of the RGTA used was that of impregnation of the tissues, for example for the case of transplants of a tissue or of an organ such as kidney, liver, heart, lung, skin, cornea, ear drum, muscles, nerves, tendons, ligaments, bones, vessels or intestins, colon, both in areas of anastomoses and in implants, bladder, etc., without this list being exhaustive. In this embodiment which can be used with respect to all tissues and grafts, the organ to be transplanted, which may be impregnated, for example either by immersing it in a solution of RGTA, or by perfusion, or by spraying or any other method known to those with ordinary skill in the art. Advantageously, the impregnation of the tissues, as mentioned above, advantageously makes it possible to recreate the tissue microenvironment. Indeed, RGTA advantageously binds specifically to the heparan-binding sites available after the lesion and induced by the harvesting of the graft or the preparation of the transplant recipient. Advantageously, this binding makes it possible to recreate a niche which promotes colonization by the cells. The preferred concentrations of RGTA were from 0.01 to 100 microgram (mg) per ml. The impregnation time was short since a few minutes are sufficient. Advantageously, an impregnation of a few hours or day(s) can make it possible to simplify the procedure since the RGTA can be added to the preserving solutions and can prove to be a protective and anti-apoptotic agent as is described in the related art (Barritault D., Caruelle J-P. BIP121532, "POLYMERES BIOCOMPATIBLES, LEUR PROCEDE DE PREPARATION ET LES COMPOSITIONS LES CONTENANT" ["BIOCOMPATIBLE POLYMERS, PROCESS FOR PREPARING SAME AND COMPOSITIONS CONTAINING SAME"]; and Yue X-L, Lehri S, Li P, Barbier-Chassèfiere V, Petit V, Huang Q-F, Albanese P, Barritault D, Caruelle J-P, Papy-Garcia D and Morin C. Insights on a new path of pre-mitochondrial apoptosis regulation by a glycosaminoglycan mimetic.; Yue X-L and al, Cell Death and Differentiation, 2009, 1-12). The tissues were then exposed to solutions or suspensions enriched, as appropriate, with cells of a desired specificity, this being before or after the implantation. It is possible to add growth factor-enriched platelet extracts or lysates to this technique.

The autologous cells were added with the graft before or after the implantation, advantageously making it possible to facilitate the colonization of host-graft junction areas and to promote the transplant engraftment. This method allows transplant engraftment, prevents necrosis and increases functional recovery.

In the examples, the platelet extracts were administered alone after having administered the RGTA or with the RGTA. In this case, the mixture was prepared with an RGTA/PRP extract ratio such that the lysate of platelets obtained from 10$^9$ platelets suspended in 1 ml of physiological saline is placed in the presence of thrombin, or at 100 mg of RGTA. At the end of the platelet degranulation, the solution was centrifuged at low speed. The supernatant containing the platelet factors and the RGTA was then administered on the lesion site.

In another embodiment, the RGTAs alone or mixed with platelet extracts (PRPs) or isolated factors were injected with the therapeutic cells.

In the examples, the administration of the RGTA was carried out at the latest at the time of the first administration of the cells, or preferably a few hours or days before. Thus, in the case of oral intakes of RGTA, it was observed that one or more daily intakes one week before the cell therapy increased the final tissue regeneration result, the preferred dose then being to drink 25 ml of the RGTA OTR4120 at 100 mg/ml in the morning before eating and in the evening before going to bed, for at least one week. When an IV or local injection of the RGTA was given, the cell therapy could be carried out within the hour following the administration of RGTA.

In the examples described below, the cells are autologous and are preferably administered on the same day as that on which they are taken.

Example 2

Example of Treatment of a Tissue Lesion with the Administration of RGTA and of Mesenchymal Stem Cells (MSCs) in a Murine Model In the present example, the mice used were 70 ten-week-old female (C57/BL6) mice from Charles River divided up into 7 groups of 10 mice, and correspond to a mouse model acknowledged in the related art.

A skin wound was made on the back of the mice using a punch 6 mm in diameter (used clinically for biopsies) and the wound was then left in the open air. Four wounds were made on each animal.

The polymer used was OTR4120 and it was administered by subcutaneous (SC) injection in a proportion of 25 microl (µl) of a solution at 100 µl at two (diametrically opposed) points. The mesenchymal stem cells (MSCs) originating from bone marrows (tibia) isolated according to conventional protocols such as those described in "A protocol for isolation and culture of mesenchymal stem cells from mouse bone marrow", Soleimani M, Nadri S. Nat Protoc. 2009;4(1):102-6 was suspended in a phosphate-buffered saline PBS at a concentration of $1 \times 10^6$ cells per ml and were injected in a proportion of 2 injections of 50 µl per wound at two points (symmetrical, orthogonal to those of the RGTA) at various times and the wound was then measured 3, 5, 7 and 10 days after the injury.

During the experiments, for each mouse, several wounds were made and a comparison was performed between:

- two injections that were diametrically opposed with respect to the wound for the RGTA,
- two injections that were diametrically opposed with respect to the wound for the MSCs, and
- four injections at the 4 cardinal points coupling the RGTA and MSCs.

Various groups of mice were defined according to the composition administered according to the abovementioned processes and are given in detail below:

Group 1 Control (Placebo): administration of physiological saline within 15 minutes following the wound/lesion.

Group 2 Administration of MSCs: 1 million MSCs per administration at 2 symmetrical points opposite to the RGTA injection sites, 24 hours after the injury after the injury.

Group 3: administration of RGTA after injury.

Group 4: administration of RGTA mixed with MSCs (co-injected).

Group 5: administration of RGTA after the injury, followed by administration of MSCs 5 minutes later.

Group 6: administration of RGTA after the injury, followed by administration of MSCs 6 hours later.

Group 7: administration of RGTA after the injury, followed by administration of MSCs 12 hours later.

Group 8: administration of RGTA after the injury, followed by administration of MSCs 24 hours later.

The table below summarizes the results regarding the wound closure kinetics measured in % on each animal according to the treatments. At time zero, the surface area of the lesion is by definition 100% for each animal, when the wound is closed the value is equal to 0%.

TABLE 1

Change in the wound as a function of time

| Group | 0 | 3 | 5 | 7 | 10 |
|---|---|---|---|---|---|
| 1-PBS | 100 | 53 +/− 15 | 29 +/− 15 | 15 +/− 10 | 5 +/− 5 |
| 2-MSCs | 100 | 38 +/− 10 | 20 +/− 5 | 10 +/− 5 | 0 |
| 3-RGTA | 100 | 40 +/− 5 | 25 +/− 5 | 10 +/− 5 | 0 |
| 4-RGTA + MSCs co-injection | 100 | 35 +/− 5 | 20 +/− 5 | 8 +/− 5 | 0 |
| 5-RGTA + MSCs 5 min | 100 | 38 +/− 5 | 20 +/− 5 | 8 +/− 5 | 0 |
| 6-RGTA + MSCs 6 h | 100 | 30 +/− 5 | 15 +/− 5 | 5 +/− 5 | 0 |
| 7-RGTA + MSCs 12 h | 100 | 15 +/− 5 | 5 +/− 5 | 0 | 0 |
| 8-RGTA + MSCs 24 h | 100 | 10 +/− 5 | 0 | 0 | 0 |

Table 1 demonstrates that the administration of MSCs and of RGTA makes it possible to improve the tissue repair and in particular makes it possible to significantly accelerate healing. In particular, the administration of the cells 24 hours after the RGTA allows closing of the wound that is much better than that obtained with the RGTA alone or the MSCs alone.

A comparable effect was obtained with cells originating from adipocytes of mice from the same litter.

Examples of Some Embodiments Observed in Clinical Practice

Many examples carried out in clinical practice, mentioned below, illustrate the effects of some embodiments. The RGTA product in its commercial form OTR4120 or CACIPLIQ® is readily accessible. On the other hand, objectification is difficult and only clinical observations document the effects of some embodiments.

Example 3

Effects of the Combined Treatment with the RGTA and The Autologous Mesenchymal Stem Cells (MSCs) in Chronic Wound Healing In these examples, patients having various types of chronic wounds of varied etiology, such as diabetic ulcers, venous ulcers, ischemic ulcers, pressure sores, burns and transplant engraftments have been experiencing therapeutic failure for months. Several treatments had been tried without success, including a local treatment with CACIPLIQ® (RGTA OTR4120) according to the manufacturers' recommendations.

This clinician was also used to combining RGTA technology with platelet extracts or carrying out cell therapies using autologous MSCs obtained by sampling 5 ml of bone marrow from the sternum of the consenting patient. The sample, having been filtered and enriched by centrifugation according to the techniques described for MSCs, were suspended in 1.5 ml of physiological saline and the cell solution was injected into the edges of the wound subcutaneously and also in the center of the wound. In all, about twelve injections of 0.1 ml around the outline of the ulcer were given (and according to the image likening the ulcer to the quarter of a clock and injecting at each position of the hours). According to this clinician, the use either of RGTA alone or of cell therapy alone did not allow wound healing.

A combined administration according to some embodiments of RGTA and cells was also carried out. CACIPLIQ® was applied locally according to the protocol recommended for the CACIPLIQ product: the solution of 5 ml containing 100 µl of CACIPLIQ® (RGTA OTR4120) was poured on to a 15×15 cm compress and the impregnated compress was applied to the well-cleaned wound for 5 minutes and then removed. The MSCs were then injected as described above (example 1) within an hour after application of the RGTA. The CACIPLIQ® was then administered locally twice a week. For a few patients, a second bone marrow sample was taken 3 weeks later, and the patients were again treated as previously with an MSC injection. The result was very rapid since closure of all the ulcers was observed in less than 6 weeks.

Another series of clinical trials was also carried out on other patients, by injection of CACIPLIQ® (RGTA) and then injection of the cells within an hour following the sampling of the cells (the time to prepare the cells). The result was then even more astonishing since all the patients were able to completely heal in less than one month. Furthermore, he even noted that some of these patients experienced closure of their wound in 15 days, even though the wound had persisted for months without any sign of improvement. Such rapidity had never been observed by this clinician, regardless of the treatment applied, in particular during treatment with CACIPLIQ® alone or the MSCs alone.

This example therefore clearly demonstrates that the composition according to some embodiments advantageously and surprisingly make it possible to effectively treat tissue lesions, in particular chronic wounds, and advantageously allows a considerable acceleration of healing.

In addition, this example clearly demonstrates that the composition according to some embodiments provide a novel solution to a problem for which no solution existed in the related art.

In addition, a comparable if not even better effect was observed on patients using co-administration of RGTA, of PRP and of cells. In one preferred embodiment, the administration of RGTA was followed by an injection of PRP and then of cells, the administration, for regulatory reasons, having been carried out during the same operating period. The RGTA was administered alone (1 ml at 100 mg/ml of OTR4120), with or sequentially to the PRP (originating from a lysate of platelets from a blood sample from the patient, for example 50 ml), with or sequentially to the mesenchymal autologous cells, for example, but without this being limited, from various tissue sources.

In another embodiment, a sample of mesenchymal stem cells was taken from the adipose tissues of the patient to be treated, by liposuction. The method for isolating the MSCs was identical to the method described in example 1 above.

In another example of treatment using the composition according to some embodiments, a patient presented with a deep wound covering part of the underneath of the foot including the large toe and including a visible area of necrosis on at least half of the underneath of the toe. There was a strong odor of decomposition in the consultation room. A first treatment by cell therapy using injections of 0.1 ml at several points around the wound for a total of 1 ml of mesenchymal cells originating directly from the bone marrow from the patient's sternum was carried out unsuccessfully, and in addition the condition of the wound had worsened. A second treatment using the administration of only CACIPLIQ (registered trademark) locally also did not make it possible to improve the wound and only made it possible to prevent a greater degradation and "to maintain" a condition of status quo regarding the progression and aggravation of the wound, thus avoiding immediate amputation. Following these failures, an injection of 0.5 ml at 5 points of 0.1 microg.ml$^{-1}$ to 100 microg.ml$^{-1}$ of the RGTA (CACIPLIQ) at the junction between the still healthy areas and the necrotic area of the toe, followed one hour later by 5 injections, each of 0.1 ml, of cells originating directly from a further sample of 0.5 ml of cells by puncture of the sternum, were given. Following the administration of the composition according to the some embodiments a regression of the wound was observed, making it possible to avoid any amputation, and going as far as complete recovery of the wound. In particular, the necrotic area was totally eliminated and then replaced with budding originating from the still healthy tissues contiguous to the wound until there was complete coverage of the wound. In this example, a single injection sequence (RGTA and then mesenchymal autologous cells) was sufficient to treat this patient and allowed closure of the patient's wound.

Example 4

Effect of the Combined Treatment with the RGTA and Cell Therapy in Bone Tissue Healing In this example, the treatment of a non union fracture placing was carried out using the composition according to some embodiments.

Likewise, the related art describes in namely an ineffective and dissuasive combination of the administration of RGTA with a cell therapy was carried out in the related art but did not make it possible to obtain any improvement in the fractures, this being after several months. The results on open wounds made it possible to obtain a notable acceleration of the healing process.

Patients with a non union bone fracture of the tibia who had not successfully improved either through application of the RGTA alone or after the administration of cells from bone marrow according to the protocols of the art described above or that described by Hernigou P, Homma Y, Flouzat-Lachaniette C H, Poignard A, Chevallier N, Rouard H. Cancer risk is not increased in patients treated for orthopaedic diseases with autologous bone marrow cell concentrate. J Bone Joint Surg Am. 2013;95:2215-21.

Patients having responded neither to the treatment with the RGTA alone nor to the treatment with autologous cells taken directly from the bone marrow were treated with the composition according to some embodiments. Surprisingly and unexpectedly, in particular in the light of the teaching of the related art, the use of the composition according to some embodiments, in particular the combination of RGTA with the cells from the bone marrow, made it possible to trigger the healing process in these patients and to obtain what no treatment had successfully obtained alone, thus showing the advantage of some embodiments. In particular, three patients experiencing therapeutic failure were treated with the composition according to the some embodiments and were able to benefit from this double treatment. In these cases, the cells from bone marrow were administered 1 h after administration of 1 ml of RGTA by local injection in the area of non union and of 1 ml of mesenchymal cells, taken by puncture of the patient's sternum and reinjected into the area of the non union bone fracture without any other treatment step.

A combination additionally including platelet extracts was also performed and gives excellent results when it is used between the administration of the RGTA and of the cells. In particular, very positive results were obtained with the administration of the RGTA, followed one hour later by the PRP and then the cells.

In this other example, the effect of the composition according to some embodiments on the bone preservation and action on the ischemic necrosis of the femur head were also studied. A treatment using the RGTA and the cells or the RGTA, PRP and cells was carried out. The patients presented with cases of early-stage femur head ischemia before deep necrosis causing considerable pain had set in. A treatment using the RGTA and the cells according to some embodiments made it possible to prevent the destruction of the femur head and the need to perform surgical procedures in order to implant a prosthesis. The treatment included or consisted of the local injection of 1 ml of RGTA OTR4131 at 10 microg.ml$^{-1}$ in the periosteal ischemic area close to the lesion, followed 30 minutes later by the local injection of 5 ml of autologous cells from bone marrow taken from the iliac fossa on the same day.

In another case, a cotreatment with PRP was carried out; the PRP was prepared from a sample of 10 ml of peripheral blood according to the usual methods and injected locally a few minutes before the cells of the sample. The results obtained via these two treatments showed a preservation of the femur head. It should be noted that, in several of these patients presenting with tissue necrosis that had already set in, there was complete disappearance of the necrosis, suggesting a process of regeneration and replacement of the necrotic tissues. The combination of the RGTA and of the autologous cells advantageously makes it possible to obtain this regeneration with a synergistic and surprising effect, improved by the injection of the PRP. In this example, the effect of the composition according to some embodiments in the treatment of bone destructions in the case of a post-infection osteonecrosis was studied.

Bone tissue destruction is a frequent consequence and a complication of the treatment of chronic wounds subsequent to osteomyelitis of infectious bacterial origin normally treated over a long period with antibiotics. The composition/method according to fee some embodiments was used and made it possible to save and to reform bone tissue. The synergistic action of the RGTA supplemented by the cell therapy enabled a regeneration of the lesioned bone tissue such that has never been observed with RGTA alone or the cell therapy alone. Several patients thus treated with several local injections of 0.1 ml of CACIPLIQ (OTR4120 at 100 microg.ml$^{-1}$) in the healthy tissue part around the necrotic area, followed by injection of the same volume of mesenchymal cells taken from the patient's sternum without any other preparation were thus able to recover bone tissue before it was completely destroyed, which would have been difficult without this therapy. It should be noted that this treatment was given while maintaining the antibiotic treatment and that, however, no integral bone regrowth was observed, the treatment making it possible to save or even to recover, but not enabling ex nihilo regrowth of an entirely destroyed bone.

Example 4

Treatment of Joint and Tendon Lesions with an Example of a Composition According to Some Embodiments The related art describes the effects of the injection of RGTA alone, in particular OTR4131, in the treatment of tendon and joint lesions in sport and race horses (Coudry V et al. Journal of Equine Veterinary Science, 2014, 34 pages 1357-1360, David Carnicer, research report "Preliminary report: ultrasonographic evolution of tendon lesions treated with RGTA in horses" école nationale vétérinaire de [national veterinary school of] Maison Alfort); the same is true for the use of cell therapy, in particular of mesenchymal cells taken from horses at the iliac fossa or more commonly the sternum (Pechayre M. and Betizeau C. S0704, AVAC Conference, 2-4 Dec. 2011. Lyon annual conference).

The PRP was also used in the same indications (http://fr.slideshare.net/dvmfun/platelet-rich-plasma-prp-therapy).

A comparative study was carried out using horses treated by combining either RGTA and the cells according to the some embodiments, the RGTA and PRP, or RGTA, PRP and cell therapy, compared with a treatment with only the cells.

In this example, the horses presented with either tendon lesions (at the level of the SDF tendon) or joint lesions (osteochondrosis dessicans, subchondral bone cyst, lesions of the meniscus). In all cases, the combined RGTA and mesenchymal cell treatment allowed a much faster recovery of the race horses (return in approximately 5-6 months, that is to say a gain of one to two months compared with the recovery time after treatment with the RGTA alone or a cell treatment alone). This recovery was evaluated in terms of the recovery from limping; a faster return to training and to prior performances for almost all the horses treated. For these horses, the RGTA was injected firstly within a week following the tendon lesion under echography. The injection of cells was carried out, as appropriate, on the same day but after that of the RGTA (most commonly approximately 30 minutes to one hour corresponding to the time required to prepare the cells). The RGTA injection was sometimes followed a few minutes later by the injection of PRP and then by the injection of the autologous cells.

The amounts of RGTA, of cells and of PRP were respectively 1 ml of OTR4131, 1.5 ml of PRP lysate (from 10 ml of blood taken) and 1 ml of autologous cells, the administration of the PRP and of the cells being carried out one hour after the first injection of RGTA.

The best results were obtained in the case of joint lesions when the cells were injected mixed with a biomaterial, such as collagen or hyaluronic acid or a combination of the two. In these cases, these products are of injectable quality in solution (used in plastic surgery for wrinkles or joints in human beings) and were directly added to the solution of cells before injection. The cell solution was then diluted approximately two-fold: 1 ml of cells and 1 ml of solution of biomaterials, preferably between 0.1 to 3 mg.ml$^{-1}$.

In another embodiment, an administration as a bolus was carried out, including either RGTA and cells, or RGTA, PRP and cells. The results obtained showed an efficacious and significantly improved treatment compared with a treatment including the administration of only one of the abovementioned elements. Moreover, even more surprising results were obtained by spacing out the administration of RGTA and of cells by a period of 30 to 60 minutes to a few hours (preferably the same).

Currently, the treatment of joint lesions and suffering in patients is performed using cell therapies and in particular by local injection of autologous mesenchymal cells originating from bone marrow or from adipose tissue.

However, this treatment does not make it possible to obtain an effective treatment and has failures. Thus, a treatment using the composition according to some embodiments via in particular the administration (injection) of RGTA into the synovial fluid, followed by the injection of autologous mesenchymal cells or of adipocytes, was carried out in several patients experiencing failure of a cell therapy alone. To do this, the amounts of RGTA and of cells were respectively 1 ml at 100 microg.ml$^{-1}$, from 1 to 5 ml of autologous cells enriched with adipocyte mesenchymal cells by centrifugation and injected on the same day, generally 30 minutes to one hour after the injection of RGTA. The timing of administration by injection of the cells was carried out within the hour following the injection of RGTA or an injection of two solutions, one of RGTA immediately followed by an injection of the cells, or the simultaneous administration of the RGTA and of the cells via a single solution.

The addition of hyaluronic acid after the injection of RGTA but before or with the injection of cells and also the combination with other biomaterials such as type 2 collagens gave even better results in certain patients.

Following this treatment, and surprisingly, the lesions and associated suffering were resorbed, advantageously enabling the patients to gradually walk again without requiring the implantation of a knee prosthesis and without pain.

In particular, in about twelve patients suffering from osteochondral lesions, very disabled in their movements and by the pain, who had previously been unsuccessfully treated with cells nor with the RGTA alone; following the abovementioned treatment, eight of them were able to recover a motor capacity by virtue of the double treatment of RGTA followed by autologous cells, clearly demonstrating the surprising and unexpected advantages of the composition according to some embodiments.

Example 5

Treatment of Digestive System Tissue Lesions with a Composition According to Some Embodiments The related art describes the properties of the RGTA on the digestive tract mucosae, buccal mucosae (Morvan et al., Am J Pathol. 2004 Feb; 164(2):739-46), gingival mucosae (Escartin et al., FASEB J. 2003 Apr; 17(6):644-51) and on ulcerations in the stomach or intestines (Meddahi et al., J Biomed Mater Res. 2002, 60(3):497-501); and also their capacity to reduce fibroses by acting on collagen synthesis, on normal or irradiated isolated cells (Alexakis C. et al., FASEB J. 2001 Jul; 15(9):1546-54) and also on biopsies from tissues from patients suffering from Crohn's disease (Alexakis C. et al., Gut. 2004 Jan; 53(1):85-90). However, no effect of RGTAs on digestive system tissue lesions, in particular regarding a possible lesion repair, has been observed or identified.

In this example, a treatment using the composition according to some embodiments, namely an RGTA and cells, was applied to a patient suffering from Crohn's disease and suffering from a perineal fistula for several years. In this example, 0.5 ml of the RGTA, used at a concentration of 100 microg.ml$^{-1}$, was injected in proximity to the fistula (0.1 ml/per injection and at 3 sites) followed, within 30 minutes of the injection, by the fraction enriched with cells originating from a 10 ml liposuction sample) (0.1 ml per injection, at two or three sites, of cells).

The administration of the composition according to some embodiments made it possible to close the perianal fistula, whereas neither the RGTA alone nor the administration of these same cells had made it possible to obtain this closure and recovery.

A second patient having undergone a surgical ablation of an epidermoid carcinoma very close to the sphincter, followed by chemoradiotherapy, who had lost the function of his sphincter was able to benefit from a local injection of RGTA OTR4120 (0.1 ml at 100 microg.ml$^{-1}$) at several sites, followed, after 30 minutes, by a local injection of autologous adipocyte cells (100 microl/injection originating from an initial liposuction volume of 10 ml). Following this administration, rapid colonization of the cells of the lesional site was observed, allowing the patient to experience a functional recovery of the sphincter, which did not seem to be difficult.

Example 6

Treatment of Tissue Lesions Including the Administration of a Composition According to Some Embodiments In these examples, there was no objectification of the additive effect combining RGTA and cell therapy, because each case was isolated and unique, which did not allow an objectification of the effect(s). The only criterion observed and capable of being studied is whether or not the patient improved after treatment.

In this example, the effect of the composition according to some embodiments in pulmonary regeneration was studied. Patients suffering from lesions of the pulmonary mucosae caused by exposure to toxic vapors from fires inhaled RGTA OTR4120 placed in a vaporizer and the autologous adipocyte cells were injected on the very same day, one hour after the inhalation. The vaporizer contained a solution of OTR4120 at 100 microg.ml$^{-1}$, and the inhalation was for 10 minutes enabling the inhalation of approximately 5 ml. Within the following half an hour, autologous cells taken on the very same day by liposuction (without concentration) were injected (5 ml, IV). This administration allowed, surprisingly and unexpectedly, a rapid and functional recovery of the patient, namely improved breathing, whereas the patient treated had been experiencing therapeutic failure for several months.

In this example, the effect of the composition according to some embodiments on lesioned tissues following the implanting of a stent was observed. To do this, an oral administration of RGTA was performed on the day of the implantation of the stent and followed, after 24 h, by the IV administration of autologous adipocyte cells (originating from a 50 ml liposuction). The oral intake of RGTA OTR4120 was in an amount of 50 ml of a solution at 100 microg.ml$^{-1}$ and was maintained for 1 month. The injection of cells was repeated after 10 days and 20 days.

Recolonization after the area lesioned after implantation of the stent was observed but not documented, showing, surprisingly, a re-endothelialization of the area of implantation of the stent, which had never been observed with the RGTA alone or the cells alone.

In this example, the effect of the composition according to some embodiments on lesioned tissues, in this case a muscle accidentally irradiated and having suffered a functional loss its function. To do this, an oral administration of RGTA was carried out, namely 25 ml at 100 mg/ml for two days followed by the administration, in the irradiated area of the muscle, of cells, namely 5 injections of 1 ml of a solution of cells originating from 50 ml of bone marrow sample taken from the iliac fossa on the same day and then enriched by centrifugation and suspended in 5 ml of physiological saline. Following the administration, an evaluation of its functional activity was carried out. Surprisingly and unexpectedly, the treatment allowed a functional motor recovery, which appeared to be difficult.

In this example, the effect of the composition according to some embodiments on the re-epithelialization of the cornea was studied. To do this, the sample of cells taken from the patient's buccal mucosae was seeded, on the same day, on to corneas locally pretreated with two drops of RGTA per cornea. This treatment made it possible to obtain repair of the lesioned tissue and in particular the effect was considerably increased by the administration of CACICOL alone.

Finally, an evaluation of the effect of an example of a composition according to some embodiments on a spinal cord lesion was also carried out. A 20-year-old patient presented with degradation of motor function following a recent lesion of the spinal cord, giving him paralysis of the lower limbs. A treatment over the course of three days using an example of a composition according to some embodiments for which the amounts of RGTA and of cells were respectively 25 ml/day of RGTA orally of a solution at 100 mg/ml of OTR4120 and local injection (in the area peripheral to the spinal cord lesion) of 1 ml, at 4 points, of cells originating from a 50 ml puncture of bone marrow from the iliac fossa. This injection was repeated at 10 and 20 days, while the daily oral intake of RGTA was maintained for a period of two months.

Unexpectedly and very positively, the patient began to recover a small amount of neuromotor function after the first three days of days of treatment and gradually a noticeable improvement as far as motor recovery.

The invention claimed is:

1. A method of using a pharmaceutical or dermatological composition as a medicament for at least one selected from the group consisting of gastric or digestive ulcers, skin wound lesions, diabetic ulcers, venous ulcers, ischemic ulcers, pressure sores and burns, joint and tendon lesions and digestive system tissue lesions, comprising:
   administering a biocompatible polymer of general formula (I) below $$A_a X_x Y_y \quad (I)$$

in which:
   A represents a glucose monomer,
   X represents an $R_1COOR_2$ group,
   Y represents an $R_7SO_3R_8$ group, in which:
      $R_1$ independently represents an aliphatic hydrocarbon-based chain which is optionally branched and/or unsaturated and which optionally contains one or more aromatic rings, $R_2$ and $R_8$ independently represent a hydrogen atom or a cation, and $R_7$ independently represents a bond, or an aliphatic hydrocarbon-based chain which is optionally branched and/or unsaturated, when $R_8$ is a cation, then the cation is at least one selected from the group consisting of lithium, sodium, potassium, rubidium and cesium, and
   the administering including administering the biocompatible polymer to a patient in need of treatment for at least one selected from the group consisting of gastric or digestive ulcers, skin wound lesions, diabetic ulcers, venous ulcers, ischemic ulcers, pressure sores and burns, joint and tendon lesions and digestive system tissue lesions;
   a represents the number of monomers,
   x represents the degree of substitution of the monomers A by groups X,
   y represents the degree of substitution of the monomers A by groups Y, and;
   administering an eukaryotic cell selected from the group consisting of mesenchymal cells, adipocyte cells and bone marrow cells, the administering the eukaryotic cell is performed 12-24 hours after the administering the biocompatible polymer; and
   the administering the biocompatible polymer is performed in a manner directed to treating at least one selected from the group consisting of:
   gastric or digestive ulcers, skin wound lesions, diabetic ulcers, venous ulcers, ischemic ulcers, pressure sores and burns, joint and tendon lesions and digestive system tissue lesions; and
   wherein the number of monomers "a" is such that the weight of the polymers of formula (I) is greater than 2000 daltons;
   wherein the degree of substitution "x" is between 20% and 150%; and
   wherein the degree of substitution "y" is between 30% and 150%.

2. The method as claimed in claim 1, wherein the biocompatible polymer also includes functional chemical groups Z, different than X and Y, capable of conferring additional biological or physicochemical properties on the polymer.

3. The method as claimed in claim 2, wherein the degree of substitution "z" of all of the monomers A by groups Z is from 0% to 50%.

4. The method as claimed in claim 2, wherein the group Z is a substance capable of conferring better solubility or lipophilicity on the polymers.

5. The method as claimed in claim 4, wherein the groups Z are identical or different and are chosen from the group including amino acids, fatty acids, fatty alcohols, ceramides, or derivatives thereof, or targeting nucleotide sequences.

6. The method as claimed in claim 1, wherein the eukaryotic cell is chosen from at least one selected from the group consisting of adult or embryonic eukaryotic cells, bone marrow cells and adipose tissue cells.

7. The method as claimed in claim 1, wherein the biocompatible polymer is administered in the treatment of at least one selected from the group consisting of gastric or digestive ulcers, skin wound lesions, diabetic ulcers, venous ulcers, ischemic ulcers, pressure sores and burns, joint and tendon lesions and digestive system tissue lesions, and:
   the biocompatible polymer is administered by at least one selected from the group consisting of:
      intravenously or intramuscularly at a dose of from 0.1 to 5 mg/kg of body weight,
      by local injection at a dose of from 1 to 100 micrograms per milliliter, orally in 2 to 5 equal intakes per day, in an amount of a daily total of from 10 microg to 5 mg/kg of body weight, sublingually before eating with a concentrated aqueous solution of from 1 to 100 mg/ml, and by administration of a solution as a nasal aerosol or spray, and wherein the eukaryotic cell is administered in the treatment of at least one selected from the group consisting of gastric or digestive ulcers, skin wound lesions, diabetic ulcers, venous ulcers, ischemic ulcers, pressure sores and burns, joint and tendon lesions and digestive system tissue lesions by injection.

8. A method of using a pharmaceutical composition comprising:

i. administering a biocompatible polymer of general formula (I) below $$A_a X_x Y_y \tag{I}$$

in which:

A represents a monomer,

X represents an $R_1 COOR_2$ group,

Y represents an $R_7 SO_3 R_8$ group, in which:

$R_1$ independently represents an aliphatic hydrocarbon-based chain which is optionally branched and/or unsaturated and which optionally contains one or more aromatic rings, $R_2$ and $R_8$ independently represent a hydrogen atom or a cation, and $R_7$ independently represents a bond, or an aliphatic hydrocarbon-based chain which is optionally branched and/or unsaturated, and when $R_8$ is a cation, then the cation is at least one selected from the group consisting of lithium, sodium, potassium, rubidium and cesium, a represents the number of monomers, x represents the degree of substitution of the monomers A by groups X, y represents the degree of substitution of the monomers A by groups Y, and;

the administering including administering the biocompatible polymer to a patient in need of treatment for at least one selected from the group consisting of gastric or digestive ulcers, skin wound lesions, diabetic ulcers, venous ulcers, ischemic ulcers, pressure sores and burns, joint and tendon lesions and digestive system tissue lesions;

ii. administering an eukaryotic cell to treat at least one selected from the group consisting of gastric or digestive ulcers, skin wound lesions, diabetic ulcers, venous ulcers, ischemic ulcers, pressure sores and burns, joint and tendon lesions and digestive system tissue lesions the administering the eukaryotic cell is performed 12-24 hours after the administering the biocompatible polymer; and the administering the biocompatible polymer is performed in a manner directed to treating at least one selected from the group consisting of:

gastric or digestive ulcers, skin wound lesions, diabetic ulcers, venous ulcers, ischemic ulcers, pressure sores and burns, joint and tendon lesions and digestive system tissue lesions.

\* \* \* \* \*